United States Patent
St. Martin et al.

(10) Patent No.: US 11,628,306 B2
(45) Date of Patent: *Apr. 18, 2023

(54) POWER MANAGEMENT FOR AN IMPLANTABLE DEVICE

(71) Applicant: Medtronic, Inc., Minneapolis, MN (US)

(72) Inventors: James J. St. Martin, Blaine, MN (US); George C. Rosar, Minneapolis, MN (US); John D. Wahlstrand, Shoreview, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 143 days.

This patent is subject to a terminal disclaimer.

(21) Appl. No.: 17/321,944

(22) Filed: May 17, 2021

(65) Prior Publication Data

US 2021/0268291 A1 Sep. 2, 2021

Related U.S. Application Data

(63) Continuation of application No. 15/473,787, filed on Mar. 30, 2017, now Pat. No. 11,013,929.

(Continued)

(51) Int. Cl.
*A61N 1/372* (2006.01)
*A61N 1/362* (2006.01)
*A61N 1/378* (2006.01)

(52) U.S. Cl.
CPC .......... *A61N 1/378* (2013.01); *A61N 1/37211* (2013.01); *A61N 1/37276* (2013.01); *A61B 2560/0204* (2013.01)

(58) Field of Classification Search
CPC ........ A61B 2560/0204; A61N 1/37211; A61N 1/37276; A61N 1/378
See application file for complete search history.

(56) References Cited

U.S. PATENT DOCUMENTS

| | | | |
|---|---|---|---|
| 5,470,341 A | 11/1995 | Kuehn | |
| 5,519,564 A | 5/1996 | Carpenter, Jr. | |

(Continued)

FOREIGN PATENT DOCUMENTS

WO 2010107608 A1 9/2010

OTHER PUBLICATIONS (PCT/US2018/019316) PCT Notification of Transmittal of the International Search Report and the Written Opinion of the International Searching Authority, dated Jun. 7, 2018, 10 pages.

(Continued)

*Primary Examiner* — Jon Eric C Morales

(74) *Attorney, Agent, or Firm* — Shumaker & Sieffert, P.A.

(57) ABSTRACT

Techniques for facilitating improved power management for an implantable device are provided. In one example, an implantable device includes a telemetry circuit and a power management circuit. The telemetry circuit is configured to facilitate a telemetry session between the implantable device and an external device. The power management circuit is configured to connect a power supply to the telemetry circuit via a first current-limiting device based on a determination that the telemetry circuit satisfies a defined criterion. The power management circuit is also configured to connect the telemetry circuit to a second current-limiting device based on a determination that the telemetry circuit is connected to the first current-limiting device for a defined period of time.

20 Claims, 11 Drawing Sheets

Related U.S. Application Data

(60) Provisional application No. 62/464,731, filed on Feb. 28, 2017.

(56) References Cited

U.S. PATENT DOCUMENTS

| | | | |
|---|---|---|---|
| 5,559,660 | A | 9/1996 | Watson et al. |
| 7,099,135 | B2 | 8/2006 | Ball et al. |
| 7,330,065 | B2 | 2/2008 | Simonson |
| 7,642,677 | B2 | 1/2010 | Harris |
| 7,813,098 | B2 | 10/2010 | Mayell |
| 3,054,604 | A1 | 11/2011 | Ryoo |
| 8,194,379 | B2 | 6/2012 | Herr et al. |
| 8,264,807 | B2 | 9/2012 | Hong et al. |
| 8,427,069 | B2 | 4/2013 | Wibben |
| 9,687,658 | B2 | 6/2017 | Wu et al. |
| 9,855,433 | B2 | 1/2018 | Shahandeh et al. |
| 9,894,691 | B1 | 2/2018 | Hellman |
| 11,013,929 | B2 * | 5/2021 | St. Martin ............. A61N 1/378 |
| 2003/0149459 | A1 | 8/2003 | Von Arx et al. |
| 2006/0164778 | A1 | 7/2006 | Beletsky et al. |
| 2012/0108922 | A1 | 5/2012 | Schell et al. |
| 2012/0172690 | A1 | 7/2012 | Anderson et al. |
| 2012/0172941 | A1 | 7/2012 | Rys |
| 2012/0274270 | A1 | 11/2012 | Dinsmoor et al. |
| 2013/0123881 | A1 | 5/2013 | Aghassian |
| 2014/0214104 | A1 | 7/2014 | Greenhut et al. |
| 2014/0330327 | A1 | 11/2014 | Thompson-Nauman et al. |
| 2015/0016005 | A1 | 1/2015 | Simonson et al. |
| 2015/0026486 | A1 | 1/2015 | Liu |
| 2015/0133951 | A1 | 5/2015 | Seifert et al. |
| 2015/0341785 | A1 | 11/2015 | Young et al. |
| 2017/0056677 | A1 | 3/2017 | Zhang et al. |
| 2018/0021589 | A1 | 1/2018 | Wu et al. |
| 2018/0243567 | A1 | 8/2018 | St. Martin et al. |

OTHER PUBLICATIONS

Prosecution History from U.S. Appl. No. 15/473,787, dated Oct. 10, 2019 through Feb. 18, 2021, 136 pp.

* cited by examiner

POWER MANAGEMENT FOR AN IMPLANTABLE DEVICE

RELATED APPLICATIONS

This application is a continuation of U.S. application Ser. No. 15/473,787, filed Mar. 30, 2017, which claims the benefit of the filing date of a U.S. Provisional Application Ser. No. 62/464,731, filed Feb. 28, 2017, both are incorporated herein in their entirety.

TECHNICAL FIELD

This disclosure relates generally to implantable devices and, more particularly, to systems, apparatus, methods and computer-readable storage media that facilitate power management for an implantable device.

BACKGROUND

Modern healthcare facilitates the ability for patients to lead healthy and full lives. Implantable medical devices (IMDs) are often utilized for such medical advances. For example, IMDs such as pacemakers, implantable cardioverter-defibrillators (ICDs), neurostimulators, and drug pumps can facilitate management of a wide range of ailments, including, but not limited to, cardiac arrhythmias, diabetes, and Parkinson's disease. Patients and medical care providers can monitor the IMD and assess a patient's current and historical physiological state to identify and/or predict impending events or conditions. This monitoring often involves frequent communication with respect to the IMD.

Implantable devices, including IMDs, are increasing in complexity while shrinking in size. One hurdle to achieving such small and highly functional devices is efficient power management of these devices. In particular, many implantable devices operate from power sources that have a limited lifespan and/or are not rechargeable. As such, after the implantable device is implanted within the human body and the lifespan of the power source has been reached, the implantable device may need to be removed. Numerous processes associated with an implantable device directly impact life of a power source of the implantable device. For example, a communication connection process between an implantable device and an external device can unnecessarily drain power from a power source of the implantable device if not properly managed. Moreover, impedance of a power source included in an implantable device may increase or decrease throughout a lifespan of the implantable device based on conditions associated with the implantable device (e.g., storage conditions of the implantable device, use conditions of the implantable device, etc.). Therefore, voltage of the power source included in the implantable device can also vary. In certain scenarios, variation of the voltage of the power source can result in a low voltage condition (e.g., a battery voltage droop) for circuitry of the implantable device. Thus, extending life of a power source of an implantable device and/or reducing occurrence of certain electrical conditions for circuitry of an implantable device by providing improved power management is highly desirable

SUMMARY

The following presents a simplified summary of one or more of the embodiments in order to provide a basic understanding of one or more of the embodiments. This summary is not an extensive overview of the embodiments described herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description may include additional or alternative embodiments beyond those described in the Summary section.

Embodiments described herein include systems, methods, apparatuses and computer-readable storage media facilitating improved power management of an implantable device. Although the term "implantable device" is used herein, it is understood that in different embodiments, the implantable device can be an IMD. In some embodiments, the implantable device is or includes an IMD. As such, "implantable device" and "IMD" can be used interchangeably herein and all such variations on embodiments are envisaged. In other embodiments, the implantable device is or includes a device configured to interact with an IMD. In these embodiments, the implantable device can be implanted within a patient or can be employed externally from or on a body of a patient. Additionally or alternatively, both the implantable device and/or the IMD can be implanted within a patient.

In embodiments described herein, an implantable device can comprise a power management circuit to control current and/or voltage provided to a telemetry circuit of the implantable device. The power management circuit can provide, for example, a soft-start sequence of current-limiting devices to control current and/or voltage provided to the telemetry circuit of the implantable device. In an embodiment, the power management circuit can control the telemetry circuit through a lifetime of the implanted device when the implantable device includes a limited power source. Furthermore, the power management circuit can determine a state of a power source (e.g., a limited power source) of the implantable device and/or can control in-rush current provided to the telemetry circuit by employing the soft-start sequence of current-limiting devices. The power management circuit can also control the telemetry circuit to improve functionality of the implantable device and/or the telemetry circuit. Additionally, the implantable device can also perform continuous monitoring of a power source of the implantable device when the telemetry circuit of the implantable device is powered-on (e.g., when the power source of the telemetry circuit provides power to the telemetry circuit). In certain embodiments, the power management circuit of the implantable device can disconnect the telemetry circuit from the power source of the implantable device when a defined voltage condition is detected.

In one embodiment, an implantable device configured to be at least partially implanted within a patient is provided. The implantable device can include: a housing configured to be implanted at least partially within the patient; a memory within the housing; circuitry, within the housing, and configured to at least one of obtain sensed physiological data associated with the patient or deliver a therapy to the patient; a telemetry circuit and a power management circuit. The telemetry circuit can be configured to facilitate a telemetry session between the implantable device and an external device. The power management circuit can be configured to connect a power supply to the telemetry circuit via a first current-limiting device based on a determination that the telemetry circuit satisfies a defined criterion. The power management circuit can also be configured to connect the telemetry circuit to a second current-limiting device based on a determination that the telemetry circuit is connected to the first current-limiting device for a defined period of time.

In various different embodiments, the defined criterion can be a first defined criterion, and the power management circuit can be further configured to disconnect the telemetry circuit from the second current-limiting device based on a determination that a power supply condition associated with the telemetry circuit satisfies a second defined criterion. In an embodiment, the first defined criterion can be associated with a telemetry session with an external device, and the second defined criterion can be a defined voltage level or a defined current level. In certain embodiments, the power management circuit can be further configured to disconnect the telemetry circuit from the second current-limiting device based on a determination that a voltage level associated with the telemetry circuit satisfies a defined voltage level. In some embodiments, the power management circuit can be further configured to disconnect the telemetry circuit from the second current-limiting device based on a determination that a current level associated with the telemetry circuit satisfies a defined current level. In certain embodiments, the defined period of time is a first defined period of time, and the power management circuit can connect the telemetry circuit to a third current-limiting device based on a determination that the telemetry circuit is connected to the second current-limiting device for a second defined period of time. In some embodiments, the first current-limiting device, the second current-limiting device and/or the third current-limiting device can be resistors or constant current sources. In an embodiment, the defined criterion can be a first defined criterion, and the power management circuit can be further configured to alter a duty cycle of the second current-limiting device based on a determination that power supply condition associated with the telemetry circuit satisfies a second defined criterion. In another embodiment, the power management circuit can be further configured to repeatedly monitor a voltage level associated with the telemetry circuit based on an initiation of a connection between the telemetry circuit and the power supply via the second current-limiting device. Additionally, in an embodiment, the power management circuit can be further configured to disconnect the power supply from the telemetry circuit based on a determination that the voltage level satisfies a defined voltage level. In yet another embodiment, the power management circuit can be further configured to disconnect the power supply from the telemetry circuit based on a determination that the telemetry circuit has failed to communicate with an external device. In some embodiments, the power management circuit can be further configured to disconnect the power supply from the telemetry circuit based on a determination that the telemetry circuit has failed to broadcast an advertising data packet. In some embodiments, the telemetry circuit can be further configured to communicate with the external device via a communication channel associated with a communication protocol utilizing a level of energy consumption that is less than a defined threshold.

In another embodiment, a method is provided. The method can include facilitating, using a telemetry circuit of an implantable device, a telemetry session between the implantable device and an external device. The method can also include connecting, using a power management circuit of the implantable device, a power supply to the telemetry circuit via a first current-limiting device based on a determination that the telemetry circuit satisfies a first defined criterion. Furthermore, the method can include connecting, using the power management circuit of the implantable device, the telemetry circuit to a second current-limiting device based on a determination that the telemetry circuit is connected to the first current-limiting device for a defined period of time.

In some embodiments, the method can include disconnecting, using the power management circuit of the implantable device, the telemetry circuit from the power supply based on determining that the telemetry circuit of the implantable device satisfies a second defined criterion. In another embodiment, the method can include altering, using the power management circuit of the implantable device, a duty cycle of the second current-limiting device in response to determining that the telemetry circuit of the implantable device satisfies a second defined criterion. In yet another embodiment, the method can include monitoring, using the power management circuit of the implantable device, a power supply condition associated with the telemetry circuit. Additionally, in some embodiments, the method can include disconnecting, using the power management circuit of the implantable device, the telemetry circuit from the power supply in response to determining that the power supply condition satisfies a defined power supply level. In some embodiments, the monitoring comprises repeatedly monitoring the power supply condition associated with the telemetry circuit.

In yet another embodiment, another method is provided. The method can include determining, using a power management circuit of an implantable device, that a telemetry circuit of the implantable device satisfies a first defined criterion. The method can also include disconnecting, using the power management circuit of the implantable device, the telemetry circuit from a power source of the implantable device, wherein the disconnecting is performed based on the determining that the telemetry circuit satisfies the first defined criterion. Furthermore, the method can include determining, using the power management circuit of the implantable device, that the telemetry circuit satisfies a second defined criterion. The method can also include connecting, using the power management circuit of the implantable device, the power source to the telemetry circuit via a first current-limiting device of the power management circuit, wherein the connecting is performed based on the determining that the telemetry circuit satisfies the second defined criterion.

In some embodiments, the method can include connecting, using the power management circuit of the implantable device, the telemetry circuit to a second current-limiting device of the power management circuit in response to a determination that the telemetry circuit is connected to the first current-limiting device for a defined period of time. In some embodiments, the determining that the telemetry circuit satisfies the first defined criterion comprises determining that a power condition associated with the telemetry circuit satisfies a defined power condition. In some embodiments, the determining that the telemetry circuit satisfies the first defined criterion comprises repeatedly monitoring an electrical node associated with the telemetry circuit. In some embodiments, the determining that the telemetry circuit satisfies a defined criterion comprises the determining that the telemetry circuit satisfies the second defined criterion comprises determining that the telemetry circuit is beginning a telemetry session with respect to an external device. In some embodiments, the determining that the telemetry circuit satisfies a defined criterion comprises the determining that the telemetry circuit satisfies the second defined criterion comprises determining that the telemetry circuit is beginning a telemetry session associated with broadcasting one or more advertising data packets.

In yet another embodiment, an apparatus is provided. The apparatus can include a telemetry circuit, a power source circuit and a power management circuit. The telemetry circuit can be configured to perform a telemetry session with respect to a device. The power source can be configured to provide power to the telemetry circuit. The power management circuit can be configured to connect the power source to the telemetry circuit via a first current-limiting device based on a determination that the telemetry circuit satisfies a defined criterion. The power management circuit can also be configured to connect the telemetry circuit to a second current-limiting device based on a determination that the telemetry circuit is connected to the power source for a defined period of time.

In some embodiments, the apparatus further can include an implantable device circuit configured to generate medical treatment data associated with the apparatus. In some embodiments, the defined criterion can be a first defined criterion, and the power management circuit can be further configured to disconnect the telemetry circuit from the power source based on a determination that a power supply condition associated with the telemetry circuit satisfies a second defined criterion. In some embodiments, the power management circuit can be further configured to repeatedly monitor the telemetry circuit based on an initiation of a connection between the telemetry circuit and the power source. In some embodiments, the telemetry circuit can be configured to communicate with the device via a communication protocol utilizing a level of energy consumption that is less than a defined threshold. In some embodiments, the apparatus can be an implantable medical device configured to be implanted at least partially within a patient.

In one or more additional embodiments, a system includes an implantable device and an external device. The implantable device can include a telemetry circuit and a power management circuit. The telemetry circuit can be configured to broadcast one or more advertising data packets. The power management circuit can be configured to connect a power source to the telemetry circuit via a first current-limiting device based on a determination that the telemetry circuit satisfies a defined criterion. The power management circuit can also be configured to connect the telemetry circuit to a second current-limiting device based on a determination that the telemetry circuit is connected to the power source for a defined period of time. The external device can be configured to perform telemetry communication with the implantable device based on the one or more advertising data packets.

In some embodiments, the power management circuit can be configured to connect the telemetry circuit to the second current-limiting device based on a determination that the first current-limiting device is connected to the power source for the defined period of time. In some embodiments, the power management circuit can be configured to alter an amount of current provided to the telemetry circuit based on the determination that the telemetry circuit is connected to the power source for the defined period of time. In some embodiments, the power management circuit can be configured to repeatedly monitor a power condition associated with the first current-limiting device and the telemetry circuit. In some embodiments, the power management circuit can be configured to disconnect the telemetry circuit from the power source based on a determination that the power condition satisfied a defined threshold value.

Other embodiments and various non-limiting examples, scenarios and implementations are described in more detail below. The following description and the drawings set forth certain illustrative embodiments of the specification. These embodiments are indicative, however, of but a few of the various ways in which the principles of the specification may be employed. Other advantages and novel features of the embodiments described will become apparent from the following detailed description of the specification when considered in conjunction with the drawings.

DETAILED DESCRIPTION

The following detailed description is merely illustrative and is not intended to limit embodiments and/or application or uses of embodiments. Furthermore, there is no intention to be bound by any expressed or implied information presented in the preceding Technical Field, Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Additionally, the following description refers to components being "connected" and/or "coupled" to one another. As used herein, unless expressly stated otherwise, the terms "connected" and/or "coupled" mean that one component is directly or indirectly connected to another component, mechanically, electrically, wirelessly, inductively or otherwise. Thus, although the figures may depict example arrangements of components, additional and/or intervening components may be present in one or more embodiments.

Figure 1:
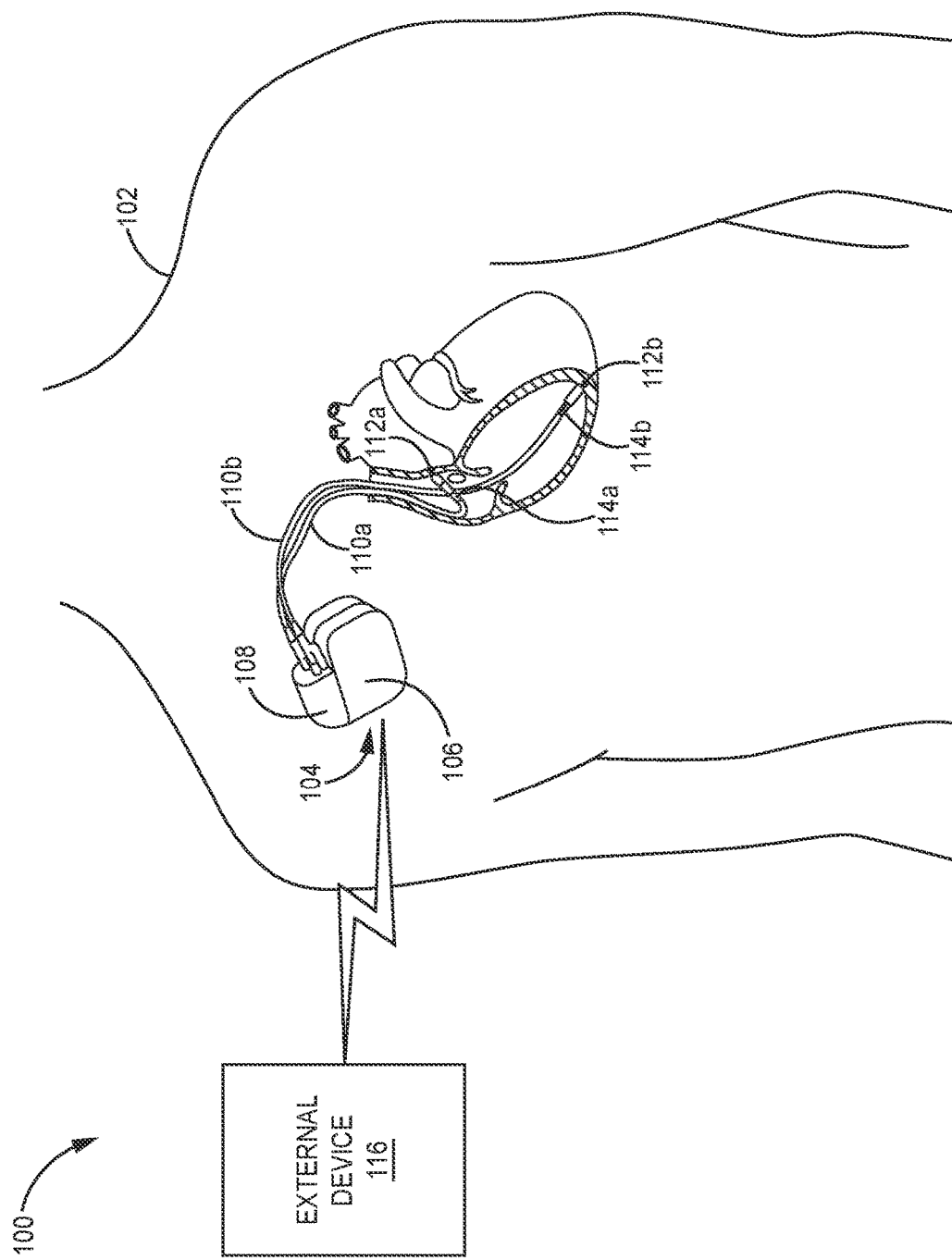
FIG. 1 illustrates a schematic diagram of an example, non-limiting implantable device telemetry system facilitating improved power management of an implantable device in accordance with one or more embodiments described herein.

With reference now to the drawings, FIG. 1 illustrates a schematic diagram of an example, non-limiting implantable device telemetry system 100 facilitating improved power management of an implantable device in accordance with one or more embodiments described herein. In the embodiment shown, implantable device telemetry system 100 includes an implantable device 104 associated with a body 102, and an external device 116. In some embodiments, as shown, the implantable device 104 can be an IMD that is implanted within the body 102. In another embodiment, the implantable device 104 can be separate from another IMD (not shown in this embodiment) that is also implanted within the body 102 and communicatively and/or electrically coupled to the IMD. However, in another embodiment, the implantable device 104 can be an instrument that is employed externally from or on the body 102 (e.g., the implantable device 104 can be a medical device that is not implanted within the body 102). In one example, the implantable device 104 can be an implantable pulse generator. In another example, the implantable device 104 can be implantable cardioverter-defibrillator. However, it is to be appreciated that the implantable device 104 can be a different type of implantable device. Embodiments of devices, apparatus and systems herein can include circuitry and/or other hardware to facilitate telemetry, power management, medical functions, diagnostic functions and/or treatment functions with respect to the implantable device 104. Additionally or alternatively, certain embodiments of devices, apparatus and systems herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described. In some embodiments, the implantable device 104 can be configured to facilitate one or more diagnostic functions or treatment functions relative to the body 102.

One or more embodiments of implantable device telemetry system 100 are described in connection with facilitating improved power management for the implantable device 104. The implantable device 104 can communicate with the external device 116 via a telemetry circuit of the implantable device 104 (e.g., telemetry circuit 202 described below in connection with FIGS. 2, 3, 4 and 5). In certain embodiments, the implantable device 104 can communicate with the external device 116 using an advertising data packet generated by the telemetry circuit of the implantable device 104.

In an embodiment, the implantable device 104 can include a power management circuit (e.g., telemetry circuit 202 described below in connection with FIGS. 2, 3, 4 and 5) to facilitate improved power management for the implantable device 104. For instance, the power management circuit can include a switch that facilitates disconnection of the telemetry circuit from a power source of the implantable device 104. The power management circuit of the implantable device 104 can be employed to mitigate power off synchronization with respect to the power source and the telemetry circuit. Furthermore, the power management circuit of the implantable device 104 can control in-rush current with respect to the telemetry circuit when the telemetry circuit is disconnected from the power source. For instance, the power management circuit of the implantable device 104 can control in-rush current with respect to voltage-voltage converter of the telemetry circuit. The power source can include one or more power supplies. In one example, the power source can be a battery that supplies power to the telemetry circuit and/or one or more other circuits of the implantable device 104. In an aspect, the power management circuit can employ the switch to disconnect the telemetry circuit from the power source via a set of current-limiting devices in response to a determination that the implantable device 104 (e.g., the telemetry circuit of the implantable device) is not communicating with the external device 116 and/or is not broadcasting an advertising data packet. For example, the power management circuit can perform a soft stop process where a first current-limiting device is disconnected from the telemetry circuit in response to a determination that telemetry circuit is to be disconnected from the power source, and a second current-limiting device is disconnected from the telemetry circuit in response to a determination that the first current-limiting device is disconnected from the telemetry circuit for a defined period of time.

The power management circuit of the implantable device 104 can also be employed to mitigate start up synchronization with respect to the power source and the telemetry circuit. Furthermore, the power management circuit of the implantable device 104 can control in-rush current with respect to the telemetry circuit when the telemetry circuit is connected to the power source. For instance, the power management circuit of the implantable device 104 can control in-rush current with respect to voltage-voltage converter of the telemetry circuit when the telemetry circuit is connected to the power source. In another aspect, the power management circuit can employ the switch to connect the telemetry circuit to the power source via a set of current-limiting devices in response to a determination that the implantable device 104 (e.g., the telemetry circuit of the implantable device) is beginning a communication process to communicate with respect to the external device 116 and/or broadcast an advertising data packet. For example, the power management circuit can perform a soft start process where the power source is connected to the telemetry circuit via a first current-limiting device in response to a determination that telemetry circuit is to be connected to the power source, and the telemetry circuit is connected to a second current-limiting device in response to a determination that the telemetry circuit is connected to the first current-limiting device for a defined period of time. The power management circuit can also provide improved system startup timing by managing power provided to the telemetry circuit. In certain embodiments, the power management circuit can also facilitate reduced frequency and/or reduced duration of recharge for the power source of the implantable device 104.

In an embodiment, the power management circuit of the implantable device 104 can monitor a power supply condition of the power source that is provided to the telemetry circuit when the telemetry is powered on. For instance, the power management circuit of the implantable device 104 can repeatedly monitor (e.g., continually monitor) a power supply condition of the power source that is provided to the telemetry circuit to enable switching off of the telemetry circuit in response to a determination that the power supply condition satisfies a defined criterion. In one example, the power management circuit of the implantable device 104 can repeatedly monitor (e.g., continually monitor) a power supply condition of the power source that is provided to the telemetry circuit to enable switching off of the telemetry circuit in response to a determination the power supply condition corresponds to a low voltage condition. Alternatively, the power management circuit of the implantable device 104 can repeatedly monitor (e.g., continually monitor) a power supply condition of the power source that is provided to the telemetry circuit to enable switching off of the telemetry circuit in response to a determination the power supply condition corresponds to a high voltage condition. In another example, the power management circuit of the implantable device 104 can repeatedly monitor (e.g., continually monitor) a power supply condition of the power source that is provided to the telemetry circuit to enable switching off of the telemetry circuit in response to a determination the power supply condition corresponds to a low current condition. Alternatively, the power management circuit of the implantable device 104 can repeatedly monitor (e.g., continually monitor) a power supply condition of the power source that is provided to the telemetry circuit to enable switching off of the telemetry circuit in response to a determination the power supply condition corresponds to a high current condition.

The telemetry circuit of the implantable device 104 can include at least one antenna to facilitate communication with other devices (e.g., the external device 116). In an embodiment, the telemetry circuit of the implantable device 104 can be configured to generate and/or broadcast an advertising data packet. An advertising data packet generated and/or broadcasted by the telemetry circuit of the implantable device 104 can be a data packet employed for advertising information to other devices (e.g., the external device 116). For example, the implantable device 104 can broadcast certain data to share with other devices (e.g., the external device 116) via an advertising data packet. In some embodiments, an advertising data packet can be a bit stream that is grouped into a set of code words. Additionally, an advertising packet can include one or more types or sections of data that include information for other devices in close proximity to the implantable device 104 that broadcasts the advertising data packet. For instance, an advertising data packet can include data associated with the implantable device 104. In an aspect, an advertising data packet can facilitate a connection between the implantable device 104 and the external device 116 that receives the advertising data packet. In certain embodiments, the advertising data packet can include a header portion and a data portion that can be read by other devices (e.g., the external device 116) to determine whether the other devices should connect to the implantable device 104. For example, the other devices (e.g., the external device 116) can establish a connection with the implantable device 104 in response to a determination that the header portion includes information relevant to the other devices (e.g., the external device 116). However, the other devices (e.g., the external device 116) can withhold from establishing a connection with the implantable device 104 in response to a determination that the header portion does not include information relevant to the other devices (e.g., the external device 116). In one example, the implantable device 104 can be implemented as an advertiser device and the external device 116 can be implemented as a scanner device.

The implantable device 104 can also include one or more devices, transducers and/or circuits that can convert information from one format to another format. In some embodiments, the implantable device 104 can include a device, a transducer and/or a circuit that can convert a signal associated with particular data for the implantable device 104 (or, in embodiments in which the implantable device 104 is an IMD, alternatively or additionally, the status of the IMD) to information for transmission by the implantable device 104 (or generally to another signal of any number of different formats suitable for reception by the external device 116).

The external device 116 can scan for the advertising data packet associated with the telemetry circuit of the implantable device 104 (e.g., without connecting to the implantable device 104). For example, the external device 116 can include a receiver that can monitor for the advertising data packet generated by the telemetry circuit of the implantable device 104. As such, if the external device 116 is within a certain range from the implantable device 104 and detects the advertising data packet, the external device 116 can obtain the data associated with the implantable device 104 without connecting to the implantable device 104.

In some embodiments, the external device 116 can establish a communication link with the implantable device 104 based on the advertising data packet. For instance, the advertising data packet can include information indicative of a request to establish the communication link with the implantable device 104. In one example, the advertising data packet can include an identifier for a particular communication channel. In another example, the advertising data packet can include an identifier for network device associated with a particular communication channel.

After establishment of the communication link between the implantable device 104 and the external device 116, in some embodiments, the external device 116 and the implantable device 104 can exchange one or more data packets. For example, after a communication link is established between the external device 116 and the implantable device 104 (e.g., based on detection by the external device 116 of an advertising data packet that includes data associated with the implantable device 104), the external device 116 can communicate with the implantable device 104 to exchange data with the implantable device 104. In a non-limiting example, the external device 116 can read data captured by the implantable device 104 (e.g., electrogram data, etc.) during the communication. The implantable device 104 can also transmit sensed physiological data, diagnostic determinations made based on the sensed physiological data, implantable device 104 performance data and/or implantable device 104 integrity data to the external device 116.

By employing the power management circuit of the implantable device 104, performance of the power source included in the implantable device 104 can be improved. For instance, power of the power source can be conserved and/or longevity of the power source can be improved by employing the power management circuit of the implantable device 104. Furthermore, the power source and/or the implantable device 104 can operate more efficiently by reducing unnecessary processing by the telemetry circuit of the implantable.

Data associated with the implantable device 104 can also be provided to a wide variety of external devices, including, but not limited to, a tablet computer associated with a patient or a physician, a smart phone associated with a patient or a physician, a medical device associated with a patient or a physician, an electronic device at a home of a patient or at an office of a physician, an off-the-shelf device purchased at a store, etc. Additionally, in some embodiments, compatibility between the implantable device 104 and external devices can be increased by allowing the data associated with the implantable device 104 to be included in an advertising data packet that can be received by any external device through the utilization of a communication protocol, such as, but not limited to, the BLUETOOTH® low energy communication protocol.

In the example shown in implantable device telemetry system 100, a person operating the external device 116 can be a patient in which the implantable device 104 is implanted. In another example, another person (e.g., such as medical caregiver) interacting with the patient in which the implantable device 104 is implanted can operate the external device 116 outside the body 102 in which the implantable device 104 is located. In various embodiments, the implantable device 104 can include any number of different types of medical devices configured to communicate with the external device 116 or another external device. The particular, size, shape, placement and/or function of the implantable device 104 may not be critical to the subject disclosure in some embodiments.

In one embodiment, as mentioned, the implantable device 104 is or includes an IMD. For example, some example IMDs can include, but are not limited to, cardiac pacemakers, cardiac defibrillators, cardiac re-synchronization devices, cardiac monitoring devices, cardiac pressure monitoring devices, spinal stimulation devices, neural stimulation devices, gastric stimulation devices, diabetes pumps, drug delivery devices, and/or any other medical devices. In various embodiments, however, the implantable device 104 can be or include any number of other types of implantable devices that are not IMDs.

For exemplary purposes, the implantable device 104 is illustrated in implantable device telemetry system 100 as an IMD implanted within the chest of a patient and configured to provide medical treatment associated with a heart disease or condition (e.g., an implantable cardioverter-defibrillator (ICD) and/or a pacemaker). In addition to the medical treatment, the implantable device 104 can also be configured to provide the data packetizing and communication operations described herein. The implantable device 104 includes a housing 106 within which electrical components and one or more power sources are housed. The electrical components can be powered via the one or more power sources. A power source (e.g., power source 206 shown in connection with FIGS. 2, 3, 4 and 5) can include, but is not limited to, a battery, a capacitor, a charge pump, a mechanically derived power source (e.g., microelectromechanical systems (MEMs) device), or an induction component. The various embodiments described herein can provide improved management of power associated with the one or more power sources.

The electrical components can vary depending on the particular features and functionality of the implantable device 104. In various embodiments, these electrical components can include, but are not limited to, one or more processors, memories, transmitters, receivers, transceivers, sensors, sensing circuitry, therapy circuitry, antennas and other components. In an embodiment, the electrical components can be formed on or within a substrate that is placed inside the housing 106. The housing 106 can be formed from conductive materials, non-conductive materials or a combination thereof. For example, housing 106 can include a conductive material, such as metal or metal alloy, a non-conductive material such as glass, plastic, ceramic, etc., or a combination of conductive and non-conductive materials. In some embodiments, the housing 106 can be a biocompatible housing (e.g., a liquid crystal polymer, etc.).

In the embodiment shown, the implantable device 104 is also an IMD and further includes leads 110*a,b* connected to the housing 106. The leads 110*a,b* extend into the heart and respectively include one or more electrodes. For example, as depicted in implantable device telemetry system 100, leads 110*a,b* each include a respective tip electrodes 112*a,b* and ring electrodes 114*a,b* located near a distal end of their respective leads 110*a,b*. When implanted, tip electrodes 112*a,b* and/or ring electrodes 114*a,b* are placed relative to or in a selected tissue, muscle, nerve or other location within the body 102 of the patient. As depicted in implantable device telemetry system 100, tip electrodes 112*a,b* are extendable helically shaped electrodes to facilitate fixation of the distal end of leads 110*a,b* to the target location within the body 102 of the patient. In this manner, tip electrodes 112*a,b* are formed to define a fixation mechanism. In other embodiments, one or both of tip electrodes 112*a,b* may be formed to define fixation mechanisms of other structures. In other instances, leads 110*a,b* may include a fixation mechanism separate from tip electrodes 112*a,b*. Fixation mechanisms can be any appropriate type, including a grapple mechanism, a helical or screw mechanism, a drug-coated connection mechanism in which the drug serves to reduce infection and/or swelling of the tissue, or other attachment mechanism.

Leads 110*a,b* are connected at a proximal end of the implantable device 104 via connector block 108. Connector block 108 may include one or more receptacles that interconnect with one or more connector terminals located on the proximal end of leads 110*a,b*. Leads 110*a,b* are ultimately electrically connected to one or more of the electrical components within housing 106. One or more conductors (not shown) extend within leads 110*a,b* from connector block 108 along the length of the lead to engage the ring electrodes 114*a,b* and tip electrodes 112*a,b*, respectively. In this manner, each of tip electrodes 112*a,b* and ring electrodes 114*a,b* is electrically coupled to a respective conductor within its associated lead bodies. For example, a first electrical conductor can extend along the length of the body of lead 110*a* from connector block 108 and electrically couple to tip electrode 112*a* and a second electrical conductor can extend along the length of the body of lead 110*a* from connector block 108 and electrically couple to ring electrode 114*a*. The respective conductors may electrically couple to circuitry, such as a therapy module or a sensing module, of the implantable device 104 via connections in connector block 108.

In one or more embodiments, the implantable device 104 is configured to deliver therapy to the heart (or other location) via the electrical conductors to one or more of electrodes 112*a,b* and 114*a,b*. In the case of pacing therapy, for example, the implantable device 104 may deliver pacing pulses via a unipolar electrode configuration, e.g., using electrodes 112*a,b* and a housing electrode of the implantable device 104. In other instances, the implantable device 104 may deliver pacing pulses via a bipolar electrode configuration, e.g., using electrodes 112*a,b* and ring electrodes 114*a,b*. Implantable device 104 may also receive sensed electrical signals on the electrical conductors from one or more of electrodes 112*a,b* and 114*a,b*. The implantable device 104 may sense the electrical signals using either a unipolar or bipolar electrode configuration.

The configuration, features and functionality of implantable device 104 are merely provided as an example. In other examples, the implantable device 104 can include more or fewer leads extending from the housing 106. For example, the implantable device 104 can be coupled to three leads, e.g., a third lead implanted within a left ventricle of the heart of the patient. In another example, the implantable device 104 can be coupled to a single lead that is implanted within the ventricle of the heart of the patient. In other embodiments, the lead may be an extravascular lead with the electrodes implanted subcutaneously above the ribcage/sternum or underneath or below the sternum. Example extravascular ICDs having subcutaneous electrodes are described in U.S. Patent Publication No. 2014/0214104 (Greenhut et al.) and U.S. Patent Publication No. 2015/0133951 (Seifert et al.), each of which is incorporated herein in its entirety. One example extravascular ICD having substernal electrodes is described in U.S. Patent Publication No. 2014/0330327 (Thompson-Nauman et al.). In some embodiments, the implantable device 104 can include other leads (e.g., atrial lead and/or left ventricular lead). As such, implantable device 104 can be used for single chamber or multi-chamber cardiac rhythm management therapy. In addition to more or fewer leads, each of the leads may include more or fewer electrodes. In instances in which the implantable device 104 is used for therapy other than pacing, (e.g., defibrillation or cardioversion), the leads can include elongated electrodes, which may, in some instances, take the form of a coil. The implantable device 104 can deliver defibrillation or cardioversion shocks to the heart via any combination of the elongated electrodes and housing electrode. As another example, the implantable device 104 can include leads with a plurality of ring electrodes, (e.g., as used in some implantable neurostimulators), without a tip electrode or with one of the ring electrodes functioning as the "tip electrode."

In another embodiment, the implantable device 104 may include no leads, as in the case of an intracardiac pacemaker or a leadless pressure sensor. In the case of an intracardiac pacemaker, the device may include a housing sized to fit wholly within the patient's heart. In one example, the housing may have a volume that is less than 1.5 cc and, more preferably, less than 1.0 cubic centimeter (cc). However, the housing may be greater than or equal to 1.5 cc in other examples. The intracardiac pacemaker includes at least two electrodes spaced apart along the outer portion of the housing for sensing cardiac electrogram signals and/or delivering pacing pulses. Example intracardiac pacemakers are described in commonly-assigned U.S. Patent Publication No. 2012/0172690 (Anderson et al.), U.S. Patent Publication No. 2012/0172941 (Kenneth), and U.S. Patent Publication No. 2014/0214104 (Greenhut et al.), each of which is incorporated herein in its entirety. In the case of a leadless pressure sensor, the device may include a housing having a fixation member and a pressure sensing component. One example of a leadless pressure sensor is described in U.S. Patent Publication No. 2012/0108922 (Schell et al.), which is incorporated herein in its entirety.

External device 116 can include any suitable computing device configured to communicate with implantable device 104. In some embodiments, the external device 116 can be a remote electronic device. For example, external device 116 can include, but is not limited to, a handheld computing device, a mobile phone, a smart phone, a tablet personal computer (PC), a laptop computer, a desktop computer, a personal digital assistant (PDA) and/or a wearable device. In some embodiments, the external device 116 can include a display that can present data associated with the implantable device 104. In another embodiment, the external device 116 can include an application and/or a program associated with the implantable device 104.

Figure 2:
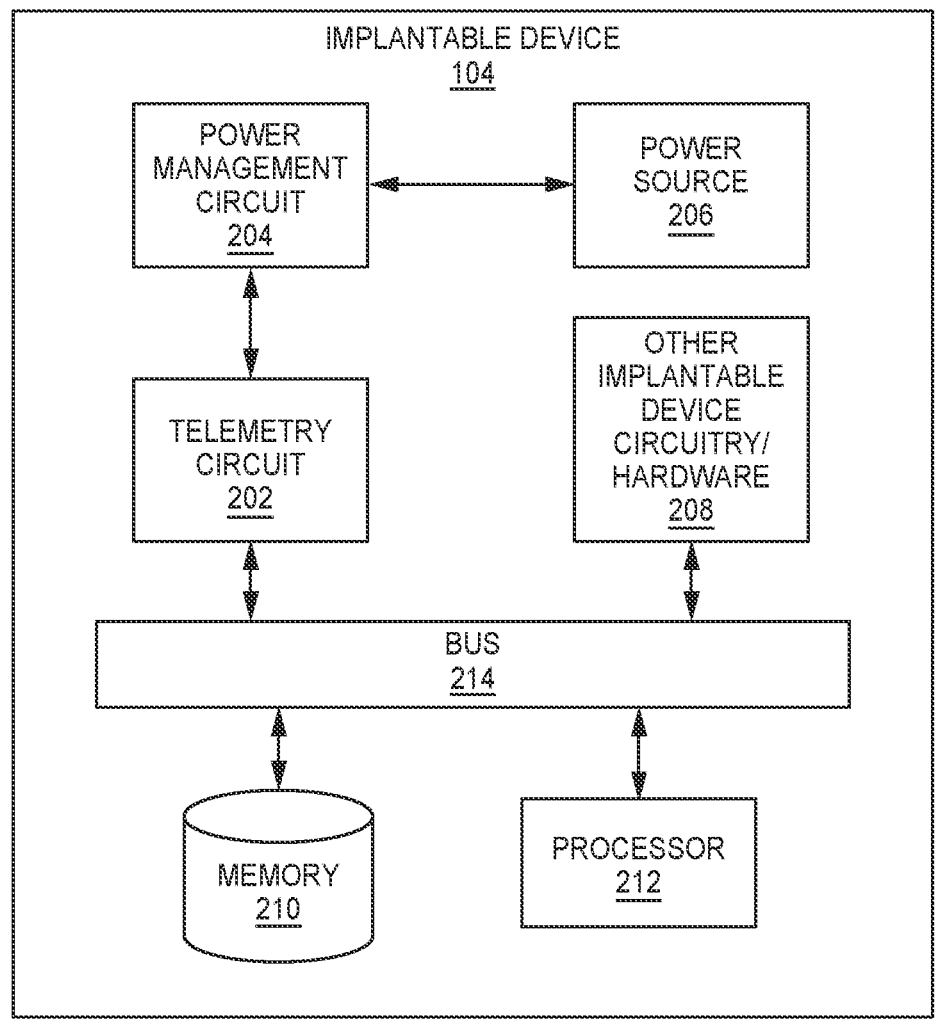
FIG. 2 illustrates a block diagram of an example, non-limiting implantable device in accordance with one or more embodiments described herein.

FIG. 2 illustrates a block diagram of an example, non-limiting medical device (e.g., implantable device 104) in accordance with one or more embodiments described herein. The implantable device 104 includes a telemetry circuit 202, a power management circuit 204, a power source 206 and/or other implantable device circuitry/hardware 208. The telemetry circuit 202 can be a hardware circuit and/or can include one or more hardware electronic components. The power management circuit 204 can also be a hardware circuit and/or can include one or more hardware electronic components. In certain embodiments, aspects of the telemetry circuit 202, the power management circuit 204 and/or the other implantable device circuitry/hardware 208 can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. Implantable device 104 can include a memory 210 for storing computer executable components and instructions. Implantable device 104 can further include a processor 212 to facilitate operation of the instructions (e.g., computer executable components and instructions) by implantable device 104. Implantable device 104 can also include a bus 214 that couples the various components of the implantable device 104, including, but not limited to, the telemetry circuit 202, the power management circuit 204, the power source 206, the other implantable device circuitry/hardware 208, the memory 210 and/or the processor 212. In an embodiment, the telemetry circuit 202 can be coupled to the bus 214 and the power management circuit 204. Furthermore, the power management circuit 204 can be implemented between the telemetry circuit 202 and the power source 206. For example, the power management circuit 204 can be coupled to the telemetry circuit 202 and the power source 206. As such, the telemetry circuit 202 can receive power from the power source 206 via the power management circuit 204. Repetitive description of like elements employed in other embodiments described herein is omitted for sake of brevity.

The telemetry circuit 202 can facilitate a telemetry session between the implantable device 104 and the external device 116. The telemetry circuit 202 can additionally or alternatively facilitate reception of data packets by the implantable device 104. The power management circuit 204 can be employed to facilitate a reduction in power employed by the telemetry circuit 202 and/or to extend a lifespan of the power source 206. For instance, the power management circuit 204 can employ a soft-start sequence associated with current-limiting devices of the power management circuit 204 to control current provided to the telemetry circuit 202 while also satisfying startup timing for a telemetry session executed by the telemetry circuit 202. In an embodiment, the power management circuit 204 can connect the power source 206 to the telemetry circuit 202 via a first current-limiting device of the power management circuit 204 based on a determination that the telemetry circuit 202 satisfies a defined criterion. In one example, the power management circuit 204 can connect the power source 206 to the telemetry circuit 202 via a first current-limiting device of the power management circuit 204 (e.g., first current-limiting device 304 shown in FIGS. 3, 4 and 5) in response to a determination that the telemetry circuit 202 is beginning a telemetry session with the external device 116. For instance, the power management circuit 204 and/or the processor 212 can determine that the telemetry circuit 202 is beginning a telemetry session with the external device 116. In one embodiment, the power management circuit 204 and/or the processor 212 can employ a schedule to determine that the telemetry circuit 202 is beginning a telemetry session with the external device 116. In another embodiment, the power management circuit 204 and/or the processor 212 can employ information generated and/or provided by the other implantable device circuitry/hardware 208 to determine that the telemetry circuit 202 is beginning a telemetry session with the external device 116. Furthermore, the power management circuit 204 can connect the telemetry circuit 202 to a second current-limiting device of the power management circuit 204 based on a determination that the telemetry circuit 202 is connected to the first current-limiting device for a defined period of time. In an alternate embodiment, the power management circuit 204 can connect the telemetry circuit 202 to a second current-limiting device of the power management circuit 204 (e.g., second current-limiting device 305 shown in FIGS. 3, 4 and 5) based on a determination that a voltage level associated with the telemetry circuit 202 and/or a current level associated with the telemetry circuit 202 satisfies a defined threshold value. It is to be appreciated that, in certain embodiments, the power management circuit 204 can employ more than two current-limiting devices and/or more than one switch to facilitate improved power management of the implantable device 104 and/or the power source 206.

In certain embodiments, the telemetry circuit 202 can include a transmitter/receiver (e.g., a transceiver). The telemetry circuit 202 can be configured to generate and/or broadcast an advertising data packet associated with the implantable device 104. In an embodiment, the telemetry circuit 202 can broadcast an advertising data packet for the implantable device 104 at a defined beaconing rate. In an aspect, the telemetry circuit 202 can include a packet generator, a transmitter, a frequency modulator, and/or other circuitry configured to generate the advertising data packet at the defined beaconing rate. The advertising data packet can be configured for transmission over an advertising communication channel. In some embodiments, the advertising communication channel can be a communication channel that is associated with a particular frequency employed for broadcast of information. In various embodiments, the advertising communication channel described herein can be a 2402 megahertz (MHz) communication channel, a 2426 MHz communication channel and/or a 2480 MHz communication channel. The particular frequencies provided are mere examples and, in other embodiments, the advertising communication channel can be located at any number of other different frequencies. The type of transmitter/receiver employed by the telemetry circuit 202 can vary depending on the type of telemetry protocol the implantable device 104 is configured to employ. In some embodiments, the telemetry circuit 202 can be configured to perform different types of telemetry protocols. In other embodiments, the telemetry circuit 202 can include a plurality of different transmitters/receivers that are respectively configured to perform different types of telemetry communication protocols. In some embodiments, rather than including a transmitter and a receiver that do not share common circuitry, the telemetry circuit 202 can include a transceiver.

Additionally, the telemetry circuit 202 can wirelessly transmit the advertising data packet associated with the implantable device 104. For instance, the telemetry circuit 202 can wirelessly transmit from the body 102 the advertising data packet associated with the implantable device 104. In one example, the telemetry circuit 202 can transmit the advertising data packet during a defined period of time. In another example, the telemetry circuit 202 can transmit the advertising data packet one or more times during a defined period of time to advertise the advertising data packet to an external device (e.g., the external device 116). In some embodiments, the telemetry circuit 202 can sequentially transmit the advertising data packet associated with the implantable device 104 via two or more advertising communication channels. For example, the telemetry circuit 202 can sequentially transmit the advertising data packet via a first advertising communication channel (e.g., a 2402 MHz communication channel), a second advertising communication channel (e.g., a 2426 MHz communication channel) and/or a third advertising communication channel (e.g., a 2480 MHz communication channel). In another example, the telemetry circuit 202 can concurrently transmit the advertising data packet associated with the implantable device 104 via two or more of the advertising communication channels. For example, the telemetry circuit 202 can concurrently transmit the advertising data packet that includes the data associated with the implantable device 104 via a first advertising communication channel (e.g., a 2402 MHz communication channel), a second advertising communication channel (e.g., a 2426 MHz communication channel) and/or a third advertising communication channel (e.g., a 2480 MHz communication channel).

The telemetry circuit 202 can transmit the advertising data packet via an advertising communication channel associated with a communication protocol utilizing lower energy consumption than a conventional communication protocol for wirelessly transmitting data. In a non-limiting example, the telemetry circuit 202 can transmit the advertising data packet via an advertising communication channel associated with a BLUETOOTH® low energy (BLE) protocol. The telemetry circuit 202 can additionally or alternatively establish, via a communication channel that different than the advertising communication channel associated with the advertising data packet, a wireless communication link with the external device 116. In one embodiment, the implantable device 104 can connect to (e.g., actively communicate with) the external device 116, transmit data directly to the external device 116 and/or receive data from the external device 116 via the wireless communication link. For example, the external device 116 can read data captured by the implantable device 104 (e.g., electrogram data) via the wireless communication link. In another example, the implantable device 104 can transmit sensed physiological data, diagnostic determinations made based on the sensed physiological data, implantable device 104 performance data and/or implantable device 104 integrity data to external device 116 via the wireless communication link.

The telemetry circuit 202 can be powered by the power source 206 to facilitate generation and/or broadcasting of the advertising data packet. The telemetry circuit 202 can receive the power associated with the power source 206 via the power management circuit 204. For instance the power management circuit 204 can manage the power provided to the telemetry circuit 202. In an aspect, the power source 206 can be, for example, a fixed power source within the implantable device 104. The power source 206 can provide power to at least the telemetry circuit 202. In an embodiment, the power source 206 can be a battery that supplies power to the telemetry circuit 202 via the power management circuit 204. However, it is to be appreciated that the power source 206 can be a different type of power source such as, for example, a capacitor, a charge pump, a mechanically derived power source (e.g., a MEMs device), an induction component, or another type of power source.

In certain embodiments, the power management circuit 204 can monitor (e.g., continually monitor) power provided to the telemetry circuit 202. For instance, the power management circuit 204 can repeatedly monitor a power supply condition associated with the telemetry circuit based on an initiation of a connection between the telemetry circuit 202 and the power source 206 via the power management circuit 204 (e.g., via the second current-limiting device of the power management circuit 204). In an embodiment, the power management circuit 204 can disconnect the telemetry circuit 202 from the power source 206 in response to a determination that a power supply condition associated with the telemetry circuit 202 satisfies a defined criterion. The power supply condition can include, for example, a voltage level associated with the telemetry circuit 202, a current level associated with the telemetry circuit 202, and/or another electrical parameter associated with the telemetry circuit 202. In one example, the power management circuit 204 can disconnect the telemetry circuit 202 from the second current-limiting device of the power management circuit 204 based on a determination that a power supply condition associated with the telemetry circuit 202 satisfies a defined voltage level. The power management circuit 204 can also alter a duty cycle of the power source 206 in response to a determination that the power supply condition satisfies a defined power supply level. For instance, the power management circuit 204 can reduce a duty cycle of the power source 206 in response to a determination that the power supply condition satisfies a defined power supply level. In one example, the power management circuit 204 can also alter a duty cycle of the power source 206 based on a determination that a voltage level associated with the telemetry circuit 202 satisfies a defined voltage level.

In another embodiment, the power management circuit 204 can disconnect the telemetry circuit 202 from the power source 206 in response to a determination that the telemetry circuit 202 has failed to communicate with the external device 116 or another device. For instance, the power management circuit 204 can disconnect the telemetry circuit 202 from the power source 206 in response to a determination that the telemetry circuit 202 is not broadcasting an advertising data packet and/or is not communicating with the external device 116. In one embodiment, the power management circuit 204 can determine whether the telemetry circuit 202 is broadcasting an advertising data packet and/or is communicating with the external device 116 based on a voltage level associated with the telemetry circuit 202. For example, the power management circuit 204 can determine that the telemetry circuit 202 is not broadcasting an advertising data packet and/or is not communicating with the external device 116 based on a determination that a voltage reading associated with the telemetry circuit 202 is below a defined threshold value. In another embodiment, the power management circuit 204 can disconnect the telemetry circuit 202 from the power source 206 by disconnecting the second current-limiting device of the power management circuit 204 from the telemetry circuit 202. In certain embodiments, after disconnecting the telemetry circuit 202 from the power source 206 for a defined period of time, the power management circuit 204 can connect the power source 206 to the telemetry circuit 202 via the first current-limiting device of the power management circuit 204, and then the power management circuit 204 can connect the telemetry circuit 202 to the second current-limiting device of the power management circuit 204 based on a determination that the telemetry circuit 202 is connected to the first current-limiting device for a defined period of time.

With reference to FIGS. 1 and 2, in some embodiments, the telemetry circuit 202 can communicate with the other implantable device circuitry/hardware 208. The other implantable device circuitry/hardware 208 can include, for example, therapy delivery circuitry, electrical sensing circuitry and/or other circuitry for medical treatment purposes associated with the implantable device 104. In an embodiment, the other implantable device circuitry/hardware 208 can be configured to sense cardiac electrical activity, detect cardiac rhythms, and/or generate electrical stimulation therapies based on sensed signals. The other implantable device circuitry/hardware 208 can be, for example, electrically coupled to tip electrodes 112a,b, ring electrodes 114a,b and/or the housing 106 to deliver electrical stimulation therapies such as cardioversion-defibrillation (CV/DF) shocks. In some examples, the other implantable device circuitry/hardware 208 can be additionally coupled to tip electrodes 112a,b and/or ring electrodes 114a,b for use in delivering therapy and/or delivering mild electrical stimulation to generate a patient alert.

The other implantable device circuitry/hardware 208 can be electrically coupled to tip electrodes 112a,b and ring electrodes 114a,b carried by leads 110a,b and housing 106, which may serve as a common or ground electrode. The other implantable device circuitry/hardware 208 can be selectively coupled to tip electrodes 112a,b, ring electrodes 114a,b and/or the housing 106 in order to, for example, monitor electrical activity of the patient's heart (e.g., electrical activity associated with tip electrodes 112a,b and/or ring electrodes 114a,b). For example, the other implantable device circuitry/hardware 208 can include detection circuitry associated with tip electrodes 112a,b and/or ring electrodes 114a,b. In one embodiment, the other implantable device circuitry/hardware 208 can be enabled to monitor one or more sensing vectors selected from the tip electrodes 112a,b and/or the ring electrodes 114a,b. For example, the other implantable device circuitry/hardware 208 can include switching circuitry for selecting which of tip electrodes 112a,b, ring electrodes 114a,b and housing 106 are coupled to sense amplifiers or other cardiac event detectors included in the other implantable device circuitry/hardware 208. Switching circuitry can include, for example, a switch array, a switch matrix, a multiplexer, or any other type of switching device suitable to selectively couple sense amplifiers to selected electrodes.

In some examples, the other implantable device circuitry/hardware 208 can include multiple sensing channels for sensing multiple electrocardiogram (ECG) sensing vectors selected from tip electrodes 112a,b, ring electrodes 114a,b and/or the housing 106. For example, the other implantable device circuitry/hardware 208 can include two sensing channels. Each sensing channel can include a sense amplifier or other cardiac event detection circuitry for sensing cardiac events, e.g., R-waves, from the received ECG signal developed across selected electrodes (e.g., tip electrodes 112a,b and/or ring electrodes 114a,b). The cardiac event detector can operate using an auto-adjusting sensing threshold set based on a peak amplitude of a currently sensed event that can decay over time. Each time the received ECG signal crosses the auto-adjusting sensing threshold outside an absolute blanking period, a cardiac sensed event signal, such as an R-wave sensed event signal, can be produced and used for detecting ventricular tachycardia (VT).

The other implantable device circuitry/hardware 208 also can be configured, for example, to detect VT episodes that may be life-threatening if left untreated (generally referred to herein as a "shockable rhythm") such as, for example, non-sinus VT, ventricular fibrillation, etc. The timing of R-wave sensed event signals received from the other implantable device circuitry/hardware 208 can be used to determine R wave to R wave intervals between cardiac sensed event signals. The other implantable device circuitry/hardware 208 can, for example, count RR intervals that fall into different rate detection zones for determining a ventricular rate or performing other rate-based assessments or interval-based assessments for detecting VT and discriminating VT from rhythms that do not require a CV/DF shock.

The other implantable device circuitry/hardware 208 can additionally or alternatively include an analog-to-digital converter that provides a digital ECG signal from one or all available sensing channels for further signal analysis for use in VT detection. A sensed ECG signal can be converted to a multi-bit digital signal by the other implantable device circuitry/hardware 208 and employed by the other implantable device circuitry/hardware 208 for performing ECG morphology analysis. Analysis of the ECG signal morphology can be performed for detecting, confirming or discriminating VT.

In an embodiment, the other implantable device circuitry/hardware 208 can include a high voltage (HV) therapy delivery circuitry including one or more HV output capacitors and, in some instances, a low voltage therapy delivery circuit. When a shockable VT rhythm is detected, the HV output capacitors can be charged to a predefined voltage level by a HV charging circuit. The other implantable device circuitry/hardware 208 can, for example apply a signal to trigger discharge of the HV capacitors upon detecting a feedback signal indicating that the HV capacitors have reached the voltage required to deliver a programmed shock energy. In this way, the other implantable device circuitry/hardware 208 can control operation of the high voltage output circuit of the other implantable device circuitry/hardware 208 to deliver high energy cardioversion/defibrillation shocks using tip electrodes 112a,b, ring electrodes 114a,b and/or the housing 106.

Each sensing channel included in the other implantable device circuitry/hardware 208 can include spike detector circuitry for detecting non-physiological electrical signal spikes present in the cardiac electrical(s) received by the other implantable device circuitry/hardware 208. The spike detector can produce a spike detect signal for use in detecting a lead issue as well as avoiding false detections of VT due to oversensing of electrical spikes that are not true R-waves. In some examples, the other implantable device circuitry/hardware 208 can be configured to detect pacing pulses delivered to the body 102. For example, bradycardia pacing pulses or anti-tachycardia pacing pulses delivered by the implantable device 104 may be detected by the spike detector of the other implantable device circuitry/hardware 208.

In certain embodiments, the external device 116 can employ telemetry communication to communicate with the telemetry circuit 202 of the implantable device 104. For example, the external device 116 can perform telemetry communication with the telemetry circuit 202 of the implantable device 104 using a telemetry communication protocol. In an embodiment, the external device 116 can scan for an advertising data packet associated with the implantable device 104 via at least one advertising communication channel. For example, the external device 116 can passively scan an advertising data packet associated with the telemetry circuit 202 of implantable device 104 without transmitting data to the implantable device 104. In various embodiments, the external device 116 can scan a first advertising communication channel (e.g., a 2402 MHz communication channel), a second advertising communication channel (e.g., a 2426 MHz communication channel) and/or a third advertising communication channel (e.g., a 2480 MHz communication channel) for an advertising data packet associated with a medical device (e.g., implantable device 104). In embodiments in which two or more channels are scanned, the particular advertising channels can be scanned in any order.

The external device 116 can also establish a communication link with the telemetry circuit 202 of the implantable device 104 via a communication channel that is different than the advertising communication channel based on a determination that a criterion associated with an identified advertising data packet is satisfied. A criterion associated with an identified advertising data packet can be, for example, that the identified advertising data packet is intended for and/or can be processed by the external device 116. For example, a criterion associated with an identified advertising data packet can be related to medical data associated with the implantable device 104.

Figure 3:
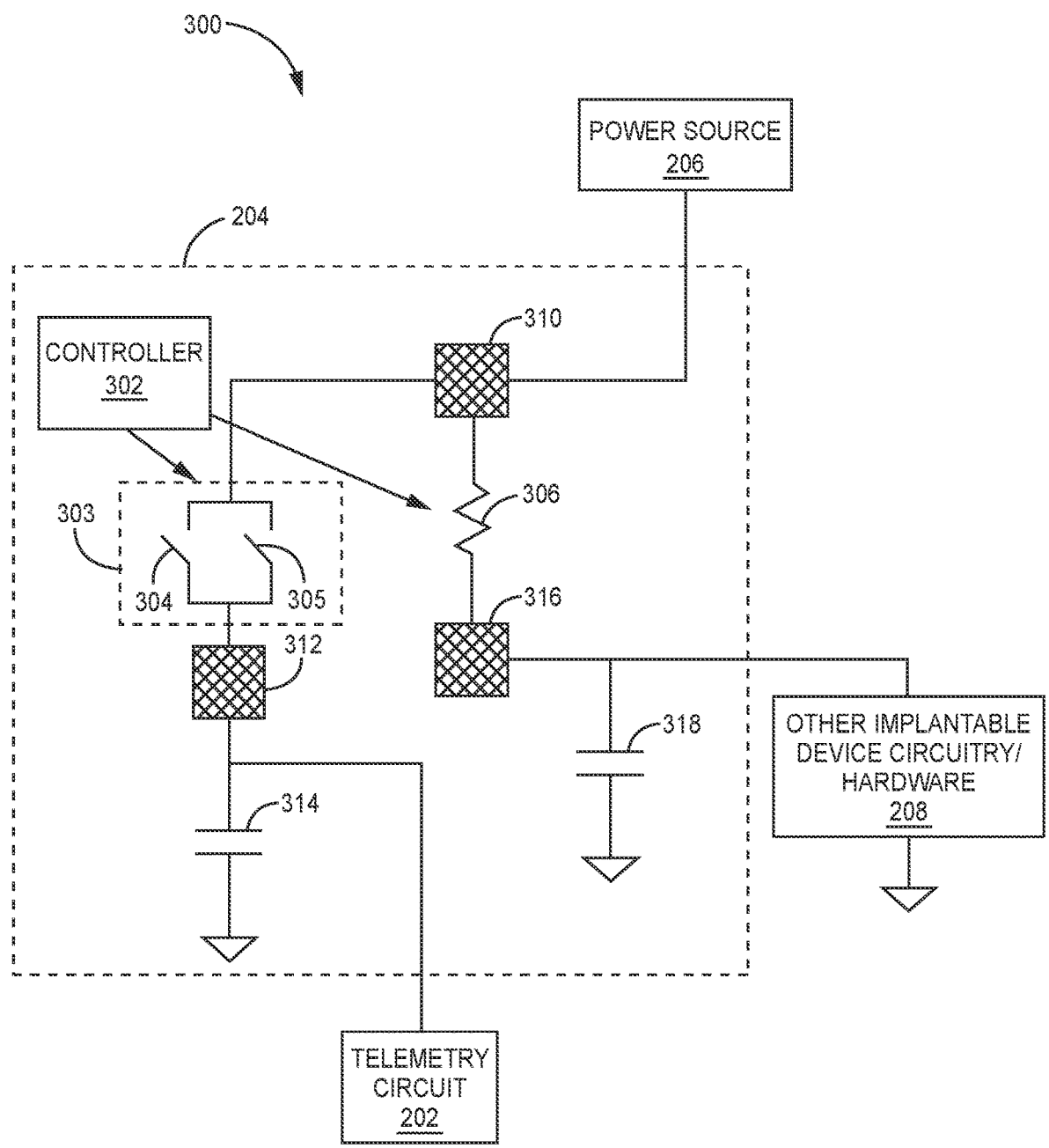
FIG. 3 illustrates a block diagram of an example, non-limiting system in accordance with one or more embodiments described herein.

FIG. 3 illustrates an example, non-limiting system 300 in accordance with one or more embodiments described herein. The system 300 includes the telemetry circuit 202, the power management circuit 204, the power source 206 and the other implantable device circuitry/hardware 208. For example, the system 300 can correspond to the telemetry circuit 202, the power management circuit 204 and the power source 206 in connection with the implantable device 104 shown in FIG. 2. Repetitive description of like elements employed in other embodiments described herein is omitted for sake of brevity.

Power source consumption of the telemetry circuit 202 can be reduced by employing the power management circuit 204. Furthermore, the power management circuit 204 can provide improved longevity of the power source 206 and/or the implantable device 104. In certain embodiments, the power management circuit 204 can also facilitate reduced frequency and/or reduced duration of recharge for the power source 206 in embodiments where the implantable device 104 is a rechargeable implantable device. The power management circuit 204 can include a controller 302, a soft-start sequence device 303 that includes a first current-limiting device 304 and a second current-limiting device 305, and a third current-limiting device 306. The power source 206 can be electrically coupled to the soft-start sequence device 303 (e.g., the first current-limiting device 304 and the second current-limiting device 305) via an electrical node 310. Furthermore, the soft-start sequence device 303 (e.g., the first current-limiting device 304 and the second current-limiting device 305) can be electrically coupled to the telemetry circuit 202 via an electrical node 312. The soft-start sequence device 303 (e.g., the first current-limiting device 304 and the second current-limiting device 305) can also be electrically coupled to a capacitor device 314 via the electrical node 312. The third current-limiting device 306 can be electrically coupled to the other implantable device circuitry/hardware 208 via an electrical node 316. The third current-limiting device 306 can also be electrically coupled to a capacitor device 318 via the electrical node 316. In an aspect, the capacitor device 314 can be employed as a decoupling capacitor to decouple at least a portion of the telemetry circuit 202 connected to the power source 206. Furthermore, the capacitor device 318 can be employed as a decoupling capacitor to decouple at least a portion of the other implantable device circuitry/hardware 208 connected to the power source 206.

Impedance of the first current-limiting device 304 can be an impedance value that is low enough to pre-charge the telemetry circuit 202 impedance such that a secondary current impulse associated with a brown out condition can be avoided when the second current-limiting device 305 is switched on. For instance, a resistance value of the first current-limiting device 304 can be approximately 1000 times greater than the second current-limiting device 305. As used herein, a "brown out condition" can be an unintended drop in voltage that can affect performance and/or a condition of the implantable device 104 and/or the telemetry circuit 202 of the implantable device 104. In a non-limiting example, the first current-limiting device 304 can comprise a resistance equal to 1 kΩ and the second current-limiting device 305 can comprise a resistance equal to 5Ω. However, it is to be appreciated that the first current-limiting device 304 and/or the second current-limiting device 305 can comprise a different resistance. In another non-limiting example, the first current-limiting device 304 can be a first resistor and the second current-limiting device 305 can be a second resistor. In yet another non-limiting example, the first current-limiting device 304 can be a first constant current source and the second current-limiting device 305 can be a second constant current source. For instance, a value of a first constant current source associated with the first current-limiting device 304 and/or a value of a second constant current source associated with the second current-limiting device 305 can be associated with a current value that prevents a voltage droop condition (e.g., a brown out condition) associated with the telemetry circuit 202. Furthermore, the first current-limiting device 304 and/or the second current-limiting device 305 can be programmable (e.g., programmable by a user). For instance, an amount of current provided by the first current-limiting device 304 and/or the second current-limiting device 305 can be programmable. Additionally or alternatively, the first current-limiting device 304 and/or the second current-limiting device 305 can be configured based on a hardware circuit of the implantable device 104 and/or firmware stored by the implantable device 104, where current restriction of the first current-limiting device 304 and/or the second current-limiting device 305 is based on droop voltage associated with the telemetry circuit 202. However, it is to be appreciated that the first current-limiting device 304 and/or the second current-limiting device 305 can be a different type of current-limiting device. The third current-limiting device 306 can also be a resistor or a constant current source. Furthermore, in certain embodiments, the third current-limiting device 306 can be programmable.

In an embodiment, the first current-limiting device 304 can be a first switch (e.g., a first low impedance switch) and the second current-limiting device 305 can be a second switch (e.g., a second low impedance switch). The electrical node 310 can receive current from the power source 206. Furthermore, the electrical node 312 can receive at least a portion of the current via the first current-limiting device 304 in response to the first current-limiting device 304 being activated by the controller 302. Alternatively, the electrical node 312 can receive at least a portion of the current via the second current-limiting device 305 in response to the second current-limiting device 305 being activated by the controller 302. Furthermore, the electrical node 312 can receive no current in response to the first current-limiting device 304 and the second current-limiting device 305 being deactivated by the controller 302. In another embodiment, the controller 302 can comprise firmware to control and/or manage the first current-limiting device 304 and the second current-limiting device 305. In one example, the controller 302 can be enabled or disabled via one or more register bits indicative of an open/close state for the first current-limiting device 304 and/or the second current-limiting device 305.

The controller 302 can connect the first current-limiting device 304 to the telemetry circuit 202 in response to a determination that the telemetry circuit 202 satisfies a defined criterion. For example, the controller 302 can connect the first current-limiting device 304 to the telemetry circuit 202 in response to a determination that the telemetry circuit 202 is beginning a telemetry session associated with broadcasting one or more advertising data packets. The controller 302 can determine whether the telemetry circuit 202 is broadcasting an advertising data packet and/or is communicating with the external device 116 based on a voltage level associated with the telemetry circuit 202. For example, the controller 302 can determine that the telemetry circuit 202 is not broadcasting an advertising data packet and/or is not communicating with the external device 116 in response to a determination that a voltage reading associated with the telemetry circuit 202 is below a defined threshold value. The first current-limiting device 304 can be employed to limit in-rush current provided to the telemetry circuit 202. Furthermore, the controller 302 can connect the second current-limiting device 305 to the telemetry circuit 202 in response to a determination that the telemetry circuit 202 is connected to the first current-limiting device 304 for a defined period of time. For example, the controller 302 can connect the second current-limiting device 305 to the telemetry circuit 202 in response to a determination that the telemetry circuit 202 has been connected to the first current-limiting device 304 for 10 milliseconds. In an alternate embodiment, the controller 302 can connect the second current-limiting device 305 to the telemetry circuit 202 in response to a determination that a voltage level associated with the telemetry circuit 202 and/or a current level associated with the telemetry circuit 202 satisfies a defined threshold value. The second current-limiting device 305 can be employed to provide a defined switch on resistance to support a defined on-current for the telemetry circuit 202. In certain embodiments, the soft-start sequence device 303 can include more than two current-limiting devices. For example, the soft-start sequence device 303 can include one or more other current-limiting devices in addition to the first current-limiting device 304 and the second current-limiting device 305. In one example, the power management circuit 204 can connect the telemetry circuit 202 to the second current-limiting device 205 based on a determination that the telemetry circuit 202 is connected to the first current-limiting device 304 for a first defined period of time, and the power management circuit 204 can connect the telemetry circuit 202 to a third current-limiting device of the soft-start sequence device 303 based on a determination that the telemetry circuit 202 is connected to the second current-limiting device 305 for a second defined period of time. The second defined period of time can be different than the first defined period of time. Alternatively, the second defined period of time can correspond to the first defined period of time. In an aspect, the first defined period of time and the second defined period of time can be determined based on a set of rules to prevent a brown out condition associated with the telemetry circuit 202 and/or to prevent a voltage droop condition associated with the telemetry circuit 202.

In an embodiment, the controller 302 can control the first current-limiting device 304 and/or the second current-limiting device 305 by employing pulse width modulation. For instance, the controller 302 can vary a duty cycle (e.g., a cycle of operation) for switching the first current-limiting device 304 and/or the second current-limiting device 305. In one example, a pulse width modulation process employed by the controller 302 can employ a pulse width modulation algorithm that powers up the telemetry circuit 202 in an acceptable time while minimizing in-rush current provided to the telemetry circuit 202. In one example, the controller 302 can control switching of the first current-limiting device 304 and/or the second current-limiting device 305 based on a first duty cycle value. In response to a determination that the first duty cycle is employed for a defined period of time, the controller 302 can modify (e.g., increase or decrease) the first duty cycle value to facilitate controlling switching of the first current-limiting device 304 and/or the second current-limiting device 305 based on a second duty cycle value. In an embodiment, the second current-limiting device 305 can be pulse width modulated to emulate current restriction transitions from the first current-limiting device 304 to the second current-limiting device 305. In certain embodiments, the other implantable device circuitry/hardware 208 can be employed to provide reduced telemetry functionality for the implantable device 104. In other embodiments, the other implantable device circuitry/hardware 208 can correspond to at least the embodiment(s) of the other implantable device circuitry/hardware 208 described in connection with FIG. 1 and/or FIG. 2. In one embodiment, the controller 302 can disconnect the telemetry circuit 202 from the power source 206 via the soft-start sequence device 303 in response to a determination that a power supply condition associated with the other implantable device circuitry/hardware 208 satisfies a defined criterion. For example, in response to a determination that a current condition for the other implantable device circuitry/hardware 208 satisfies a defined current value and/or that voltage provided to the telemetry circuit 202 is not sufficient for communicating with an external device (e.g., the external device 116), the controller 302 can disconnect the telemetry circuit 202 from the power source 206 via the soft-start sequence device 303 in order to provide current to one or more circuits (e.g., "life sustaining" circuitry) associated with the other implantable device circuitry/hardware 208. In a non-limiting example, the controller 302 can be turned on for one cycle (e.g., a given time period such as, for example, 100 μsec) and shut off for 255 cycles. In certain embodiments, the controller 302 can employ a counter to facilitate determination of cycles for the controller 302. For example, the first current-limiting device 304 and/or the second current-limiting device 305 can be shut off for 255 cycles as determined by an 8-bit counter initially set to 255, where the 8-bit counter is decreased by n (e.g., where n equals 1) for each iteration through a counter loop for the 8-bit counter, and after m cycles through the counter loop, where m is a positive integer, the controller 302 can remain in an on-position. Therefore, by employing the power management circuit 204 as more fully disclosed herein, utility and life of the power source 206 and/or the implantable device 104 can be maximized. Moreover, performance of the implantable device 104 can be improved by employing the power management circuit 204 as more fully disclosed herein.

Figure 4:
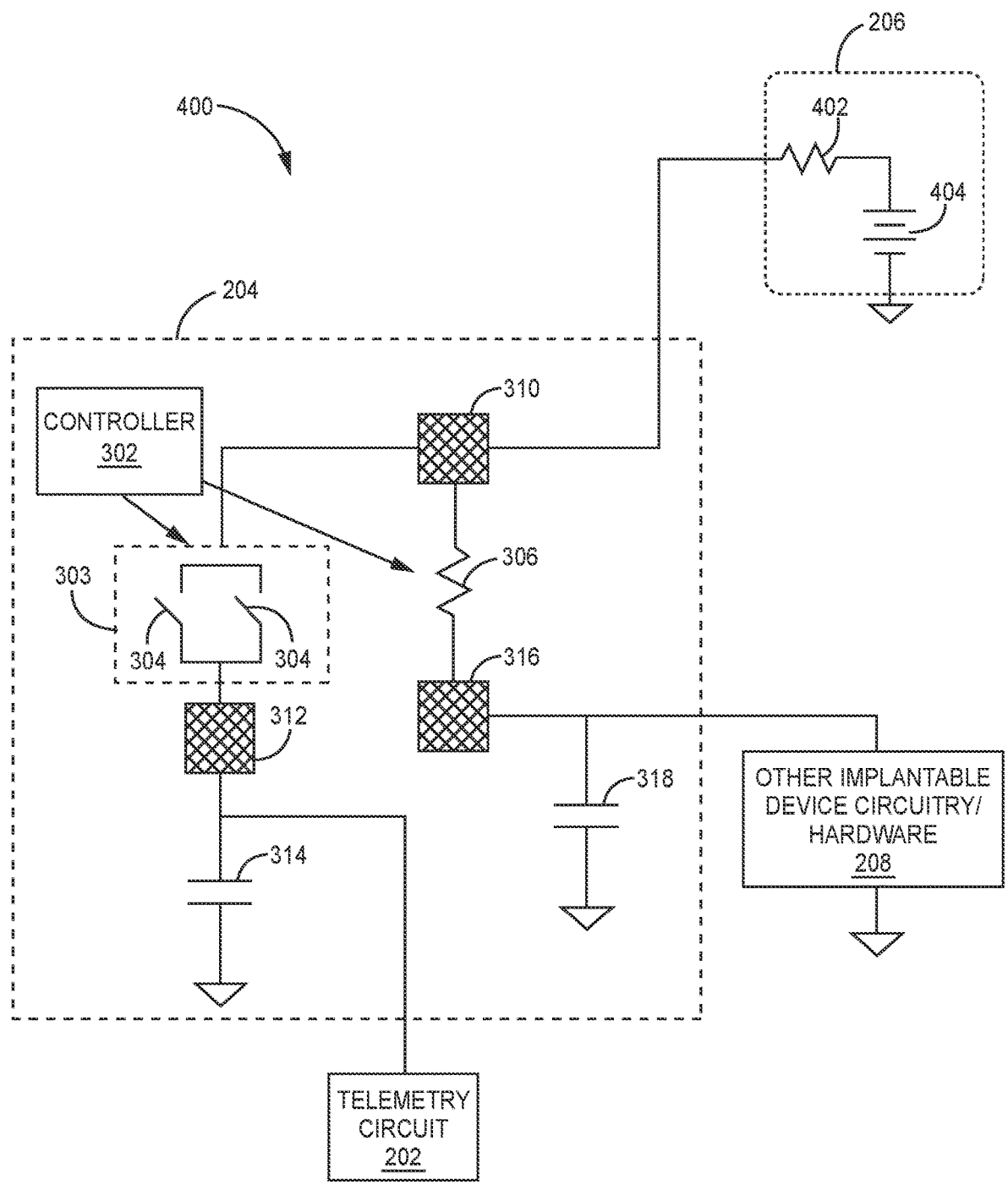
FIG. 4 illustrates a block diagram of another example, non-limiting system in accordance with one or more embodiments described herein.

FIG. 4 illustrates an example, non-limiting system 400 in accordance with one or more embodiments described herein. The system 400 includes the telemetry circuit 202, the power management circuit 204, the power source 206, and the other implantable device circuitry/hardware 208. For example, the system 400 can correspond to the telemetry circuit 202, the power management circuit 204 and the power source 206 in connection with the implantable device 104 shown in FIG. 2. In an embodiment, the power management circuit 204 can include the controller 302, the soft-start sequence device 303 (e.g., the first current-limiting device 304 and the second current-limiting device 305), the third current-limiting device 306, the capacitor device 314 and/or the capacitor device 318. Repetitive description of like elements employed in other embodiments described herein is omitted for sake of brevity.

In the embodiment shown in FIG. 4, the power source 206 can include a current-limiting device 402 and an energy source 404. For example, the energy source 404 can be a battery energy source that provides power to the telemetry circuit 202 via the power management circuit 204. In another example, the energy source 404 can be a capacitor or a charge pump that stores energy and provides the stored energy to the telemetry circuit 202 via the power management circuit 204. In yet another example, the energy source 404 can be a mechanically derived power source (e.g., a MEMs device) that that provides power to the telemetry circuit 202 via the power management circuit 204. However, it is to be appreciated that the energy source 404 can be a different type of energy source. In an aspect, the energy source 404 can be a direct current (DC) energy source that provides DC voltage and/or DC current to the telemetry circuit 202 via the power management circuit 204. Alternatively, the energy source 404 can be an alternating current (AC) energy source that provides AC voltage and/or AC current to the telemetry circuit 202 via the power management circuit 204. The current-limiting device 402 can reduce current provided by the energy source 404. For instance, the current-limiting device 402 can reduce current provided by the energy source 404 so that current received by the electrical node 310 of the power management circuit 204 is less than current provided by the energy source 404.

Figure 5:
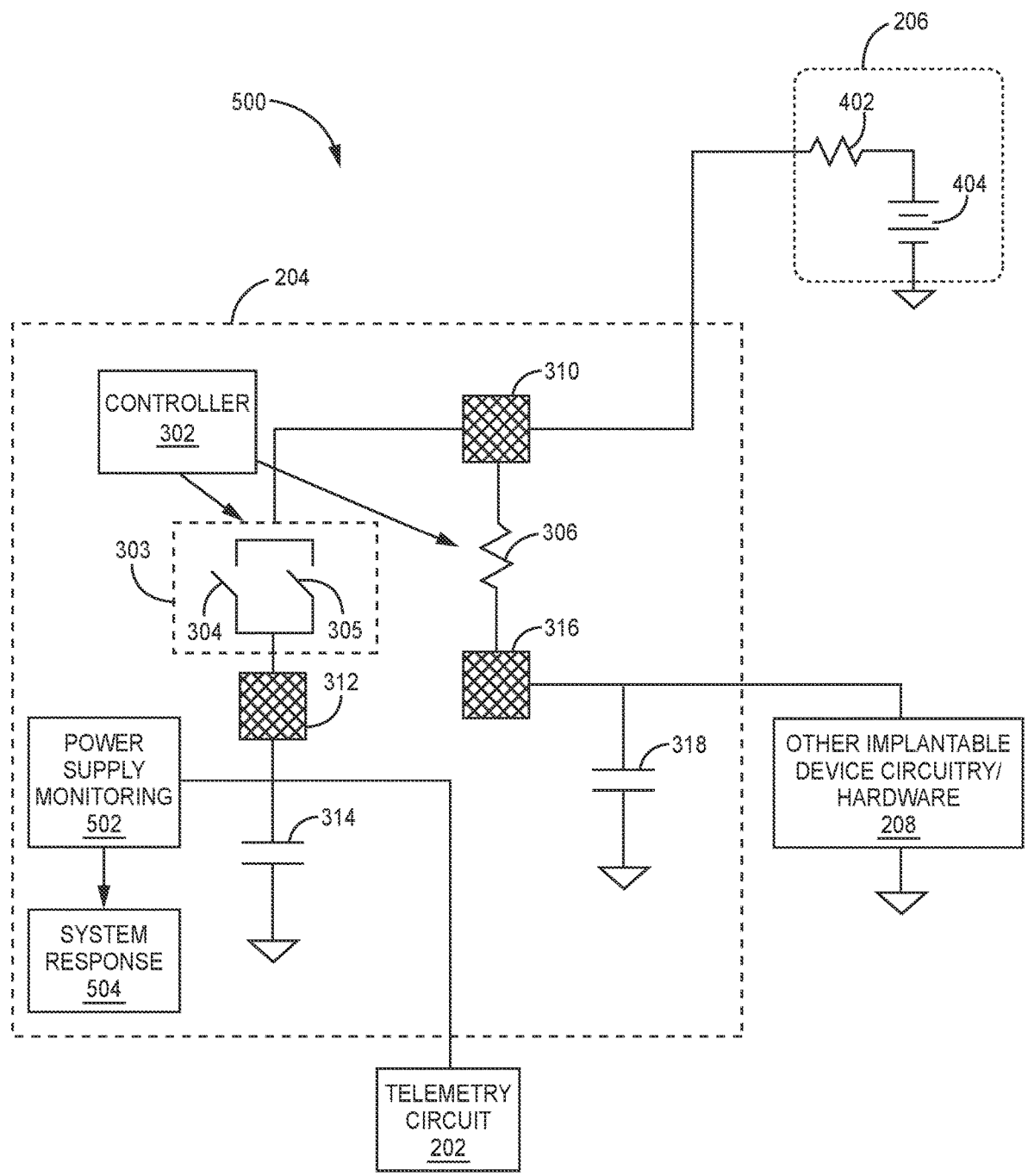
FIG. 5 illustrates a block diagram of yet another example, non-limiting system in accordance with one or more embodiments described herein.

FIG. 5 illustrates an example, non-limiting system 500 in accordance with one or more embodiments described herein. The system 500 includes the telemetry circuit 202, the power management circuit 204, the power source 206, and the other implantable device circuitry/hardware 208. For example, the system 500 can correspond to the telemetry circuit 202, the power management circuit 204 and the power source 206 in connection with the implantable device 104 shown in FIG. 2. In the embodiment shown in FIG. 5, the power management circuit 204 can include the controller 302, the soft-start sequence device 303 (e.g., the first current-limiting device 304 and the second current-limiting device 305), the third current-limiting device 306, the capacitor device 314, the capacitor device 318, power supply monitoring 502 and system response 504. In another embodiment, the power source 206 can include the current-limiting device 402 and the energy source 404. In certain embodiments, the controller 302 can include the power supply monitoring 502 and/or the system response 504. Repetitive description of like elements employed in other embodiments described herein is omitted for sake of brevity.

Embodiments of the power supply monitoring 502 and/or the system response 504 can include circuitry and/or other hardware to facilitate monitoring of a power condition associated with the telemetry circuit 202. Additionally or alternatively, certain embodiments of the power supply monitoring 502 and/or the system response 504 can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

The power supply monitoring 502 can monitor a power supply condition for power provided to the telemetry circuit 202. For instance, the power supply monitoring 502 can monitor a power supply condition associated with the electrical node 312. A power supply condition associated with the electrical node 312 can include, for example, a voltage associated with the electrical node 312, a current associated with the electrical node 312, and/or another electrical characteristic associated with the electrical node 312. In an embodiment, the power supply monitoring 502 can repeatedly monitor (e.g., continually monitor) a power supply condition associated with the electrical node 312. For instance, the power supply monitoring 502 can repeatedly monitor (e.g., continually monitor) a power supply condition associated with the electrical node 312 based on an initiation of a connection between the telemetry circuit 202 and the power source 206 via the power management circuit 204 (e.g., via the first current-limiting device 304 and/or the second current-limiting device 305). In an embodiment, the power supply monitoring 502 can employ a comparator device to repeatedly monitor (e.g., continually monitor) the power supply condition associated with the electrical node 312. For instance, the comparator device of the power supply monitoring 502 can compare a power supply value associated with the electrical node 312 to a threshold power supply value. In response to a determination by the power supply monitoring 502 that the power supply condition associated with the electrical node 312 satisfies a defined criterion, the system response 504 can enable switching off of the telemetry circuit 202. For example, in response to a determination by the power supply monitoring 502 that the power supply condition corresponds to a low voltage condition associated with the electrical node 312, the system response 504 can enable switching off of the telemetry circuit 202. In another example, in response to a determination by the power supply monitoring 502 that the power supply condition corresponds to a high current condition associated with the electrical node 312, the system response 504 can enable switching off of the telemetry circuit 202. In yet another example, in response to a determination by the power supply monitoring 502 that the power supply condition corresponds to a low current condition associated with the electrical node 312, the system response 504 can enable switching off of the telemetry circuit 202. In yet another example, in response to a determination by the power supply monitoring 502 that the power supply condition corresponds to a high current condition associated with the electrical node 312, the system response 504 can enable switching off of the telemetry circuit 202.

In an alternate embodiment, in response to a determination by the power supply monitoring 502 that the power supply condition associated with the electrical node 312 satisfies a defined criterion, the system response 504 can alter (e.g., increase or decrease) a duty cycle for switching the first current-limiting device 304 and/or the second current-limiting device 305 via the controller 302. For example, in response to a determination by the power supply monitoring 502 that the power supply condition corresponds to a low voltage condition associated with the electrical node 312, the system response 504 can alter a duty cycle for switching the first current-limiting device 304 and/or the second current-limiting device 305 via the controller 302. In another example, in response to a determination by the power supply monitoring 502 that the power supply condition corresponds to a high current condition associated with the electrical node 312, the system response 504 can alter a duty cycle for switching the first current-limiting device 304 and/or the second current-limiting device 305 via the controller 302. In yet another example, in response to a determination by the power supply monitoring 502 that the power supply condition corresponds to a low current condition associated with the electrical node 312, the system response 504 can alter a duty cycle for switching the first current-limiting device 304 and/or the second current-limiting device 305 via the controller 302. In yet another example, in response to a determination by the power supply monitoring 502 that the power supply condition corresponds to a high current condition associated with the electrical node 312, the system response 504 can alter a duty cycle for switching the first current-limiting device 304 and/or the second current-limiting device 305 via the controller 302. In an embodiment, in response to a determination by the power supply monitoring 502 that the power supply condition associated with the electrical node 312 satisfies a defined criterion, the system response 504 can alter (e.g., increase or decrease) a duty cycle for the second current-limiting device 305 to emulate a current restriction between the first current-limiting device 304 and the second current-limiting device 305 so that a secondary current spike is avoided when the second current-limiting device 305 is engaged.

FIGS. 6, 7, 8, 9 and 10 illustrate flow diagrams of example, non-limiting methods facilitating improved power management of an implantable device in accordance with one or more embodiments described herein. While, for purposes of simplicity of explanation, the methodologies are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated statuses or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

Figure 6:
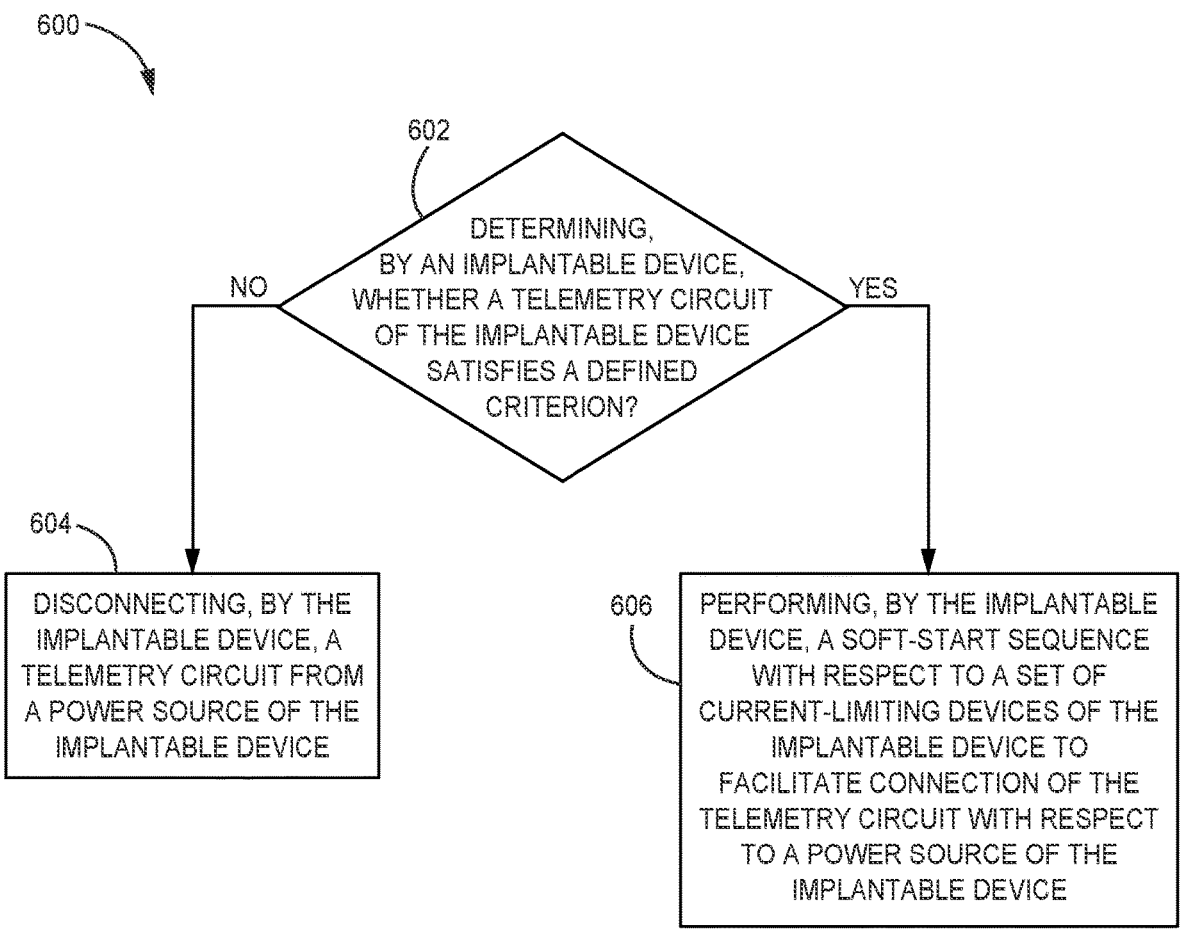
FIGS. 6, 7, 8, 9 and 10 illustrate flow diagrams of example, non-limiting methods facilitating improved power management of an implantable device in accordance with one or more embodiments described herein.

Referring now to FIG. 6, shown is a flow diagram of an example method 600 facilitating improved power management of an implantable device in accordance with one embodiment. In some embodiments of method 600, an implantable device (e.g., implantable device 104) employs a power management circuit (e.g., power management circuit 204) in connection with a telemetry circuit (e.g., telemetry circuit 202) and/or a power source (e.g., power source 206) to facilitate improved power management of the implantable device. Repetitive description of like elements employed in other embodiments described herein is omitted for sake of brevity.

At 602, it can be determined by an implantable device (e.g., by the power management circuit 204) whether a telemetry circuit of the implantable device satisfies a defined criterion. For example, it can be determined whether telemetry circuit of the implantable device is beginning a telemetry session with respect to an external device. If no, method 600 can proceed to 604. If yes, method 600 can proceed to 606. At 604, a telemetry circuit can be disconnected from a power source of the implantable device by the implantable device (e.g., using the power management circuit 204). For example, a power management circuit implemented between the power source and the telemetry circuit can disconnect a set of current-limiting devices from the telemetry circuit. At 606, a soft-start sequence with respect to a set of current-limiting devices of the implantable device can be performed by the implantable device (e.g., by the power management circuit 204) to facilitate connection of the telemetry circuit with respect to a power source of the implantable device. For example, a first current-limiting device from the set of current-limiting devices can be connected to the telemetry circuit to allow current from the power source to be provided to the telemetry circuit. Then, in response to a determination that the first current-limiting device is connected to the telemetry circuit for a defined amount of time, a first current-limiting device from the set of current-limiting devices can be connected to the telemetry circuit to allow a defined amount of current to be provided to the telemetry circuit (e.g., a defined amount of current to allow a telemetry session to be executed by the telemetry circuit). In an aspect, the soft-start sequence of the set of current-limiting devices of the implantable device can be performed in response to a determination that telemetry circuit is disconnected from the power source for a defined period of time.

Figure 7:
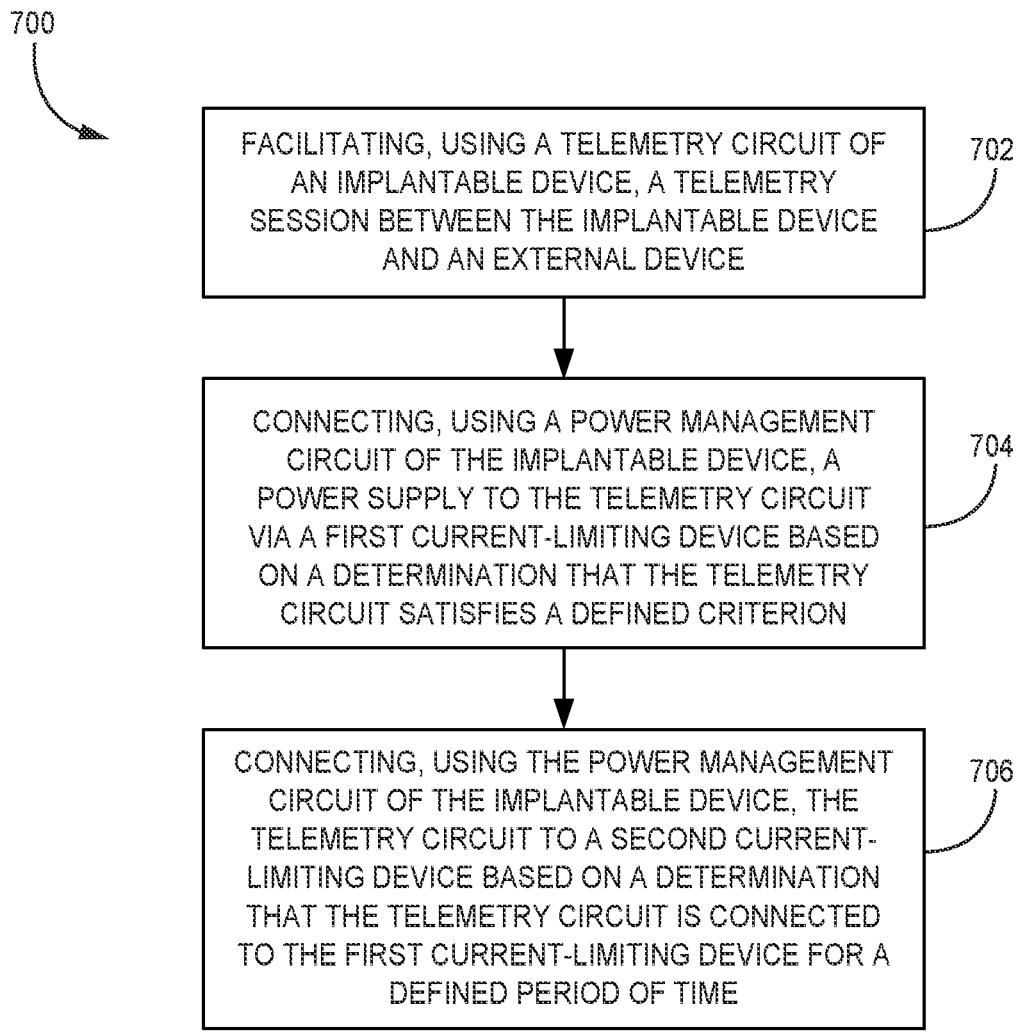

Referring now to FIG. 7, shown is a flow diagram of an example method 700 facilitating improved power management of an implantable device in accordance with another embodiment. In some embodiments of method 700, an implantable device (e.g., implantable device 104) employs a power management circuit (e.g., power management circuit 204) in connection with a telemetry circuit (e.g., telemetry circuit 202) and/or a power source (e.g., power source 206) to facilitate improved power management of the implantable device. Repetitive description of like elements employed in other embodiments described herein is omitted for sake of brevity.

At 702, a telemetry session between an implantable device and an external device can be facilitated using a telemetry circuit of the implantable device (e.g., using the telemetry circuit 202). For example, the telemetry circuit can broadcast one or more advertising data packets. In another example, the telemetry circuit can communicate with the external device via one or more data packets.

At 704, using a power management circuit of the implantable device (e.g., using the power management circuit 204), a power supply can be connected to the telemetry circuit via a first current-limiting device based on a determination that the telemetry circuit satisfies a defined criterion. For example, the power supply can be connected to the telemetry circuit via the first current-limiting device in response to a determination that the telemetry session is initiated.

At 706, using the power management circuit of the implantable device (e.g., using the power management circuit 204), the telemetry circuit can be connected to a second current-limiting device based on a determination that the telemetry circuit is connected to the first current-limiting device for a defined period of time. For example, resistance for current provided to the telemetry circuit can be modified in response to a determination that that the telemetry circuit is connected to the first current-limiting device for a defined period of time.

Figure 8:
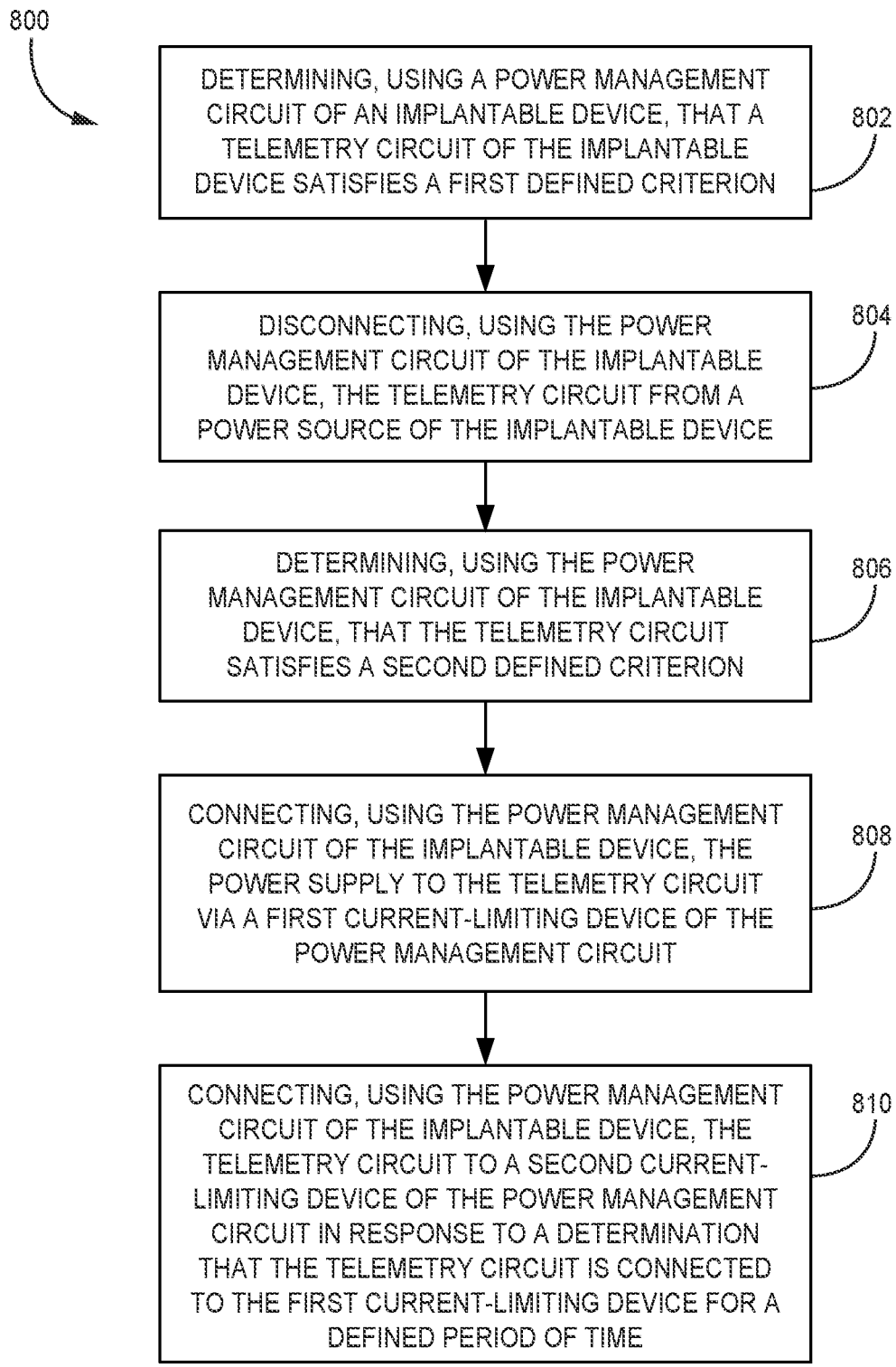

Referring now to FIG. 8, shown is a flow diagram of an example method 800 facilitating improved power management of an implantable device in accordance with yet another embodiment. In some embodiments of method 800, an implantable device (e.g., implantable device 104) employs a power management circuit (e.g., power management circuit 204) in connection with a telemetry circuit (e.g., telemetry circuit 202) and/or a power source (e.g., power source 206) to facilitate improved power management of the implantable device. Repetitive description of like elements employed in other embodiments described herein is omitted for sake of brevity.

At 802, it can be determined, using a power management circuit of an implantable device (e.g., using the power management circuit 204), that a telemetry circuit of the implantable device satisfies a first defined criterion. For example, it can be determined that the telemetry circuit is not performing a telemetry session related to broadcasting one or more data packets and/or communicating with respect to an external device. In an embodiment, it can be determined that a voltage level associated with the telemetry circuit is less than a defined voltage value.

At 804, the telemetry circuit can be disconnected from a power source of the implantable device using the power management circuit of the implantable device (e.g., using the power management circuit 204). For example, one or more current-limiting devices of the power management circuit can be disconnected from the telemetry circuit.

At 806, it can be determined, using the power management circuit of the implantable device (e.g., using the power management circuit 204), that the telemetry circuit satisfies a second defined criterion. For example, it can be determined that a telemetry session (e.g., a telemetry session related to broadcasting one or more data packets and/or communicating with respect to an external device) is being initiated by the telemetry circuit.

At 808, using the power management circuit of the implantable device (e.g., using the power management circuit 204), the power source can be connected to the telemetry circuit via a first current-limiting device of the power management circuit. For example, a first current-limiting device associated with a first resistance can be connected to the telemetry circuit.

At 810, using the power management circuit of the implantable device (e.g., using the power management circuit 204), the telemetry circuit can be connected to a second current-limiting device of the power management circuit in response to a determination that the telemetry circuit is connected to the first current-limiting device for a defined period of time. For example, a second current-limiting device associated with a second resistance that is different than the first resistance can be connected to the telemetry circuit in response to a determination that the telemetry circuit is connected to the first current-limiting device for a defined period of time.

Figure 9:
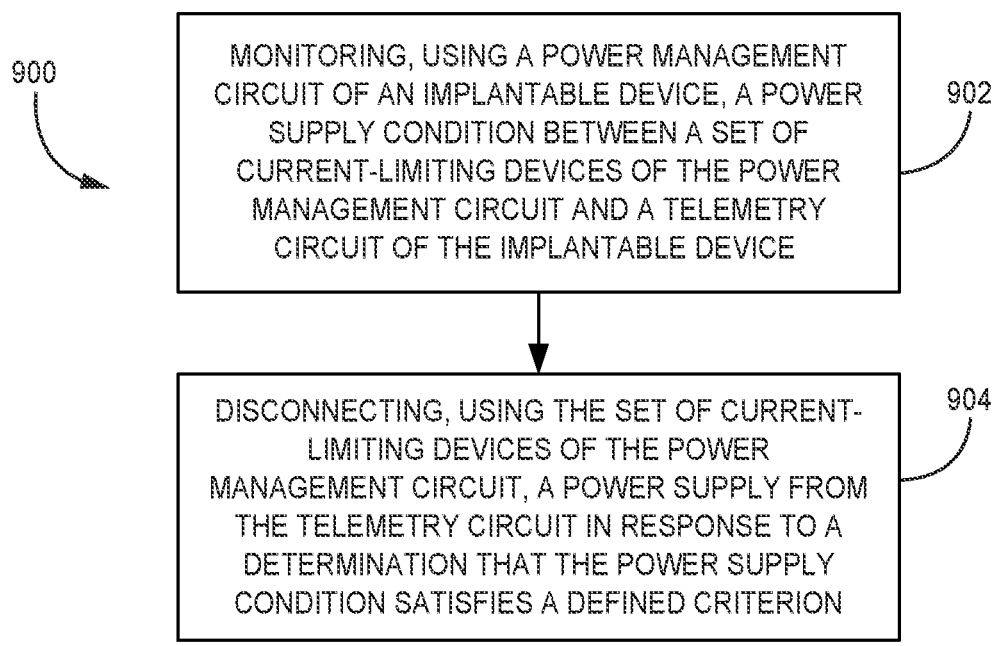

Referring now to FIG. 9, shown is a flow diagram of an example method 900 facilitating improved power management of an implantable device in accordance with yet another embodiment. In some embodiments of method 900, an implantable device (e.g., implantable device 104) employs a power management circuit (e.g., power management circuit 204) in connection with a telemetry circuit (e.g., telemetry circuit 202) and/or a power source (e.g., power source 206) to facilitate improved power management of the implantable device. Repetitive description of like elements employed in other embodiments described herein is omitted for sake of brevity.

At 902, using a power management circuit of an implantable device (e.g., using the power management circuit 204), a power supply condition between a set of current-limiting devices of the power management circuit and a telemetry circuit of the implantable device is monitored. For example, a power supply condition between the set of current-limiting devices of the power management circuit and the telemetry circuit of the implantable device can be repeatedly monitored. The power supply condition can include, for example, a voltage condition, a current condition and/or another electrical characteristic.

At 904, using the set of current-limiting devices of the power management circuit (e.g., using the first current-limiting device 304 and the second current-limiting device 305), a power supply from the telemetry circuit is disconnected in response to a determination that the power supply condition satisfies a defined criterion. For example, the power supply can be disconnected from the telemetry circuit in response to a determination that the power supply condition is above or below a defined threshold value for the power supply condition.

Figure 10:
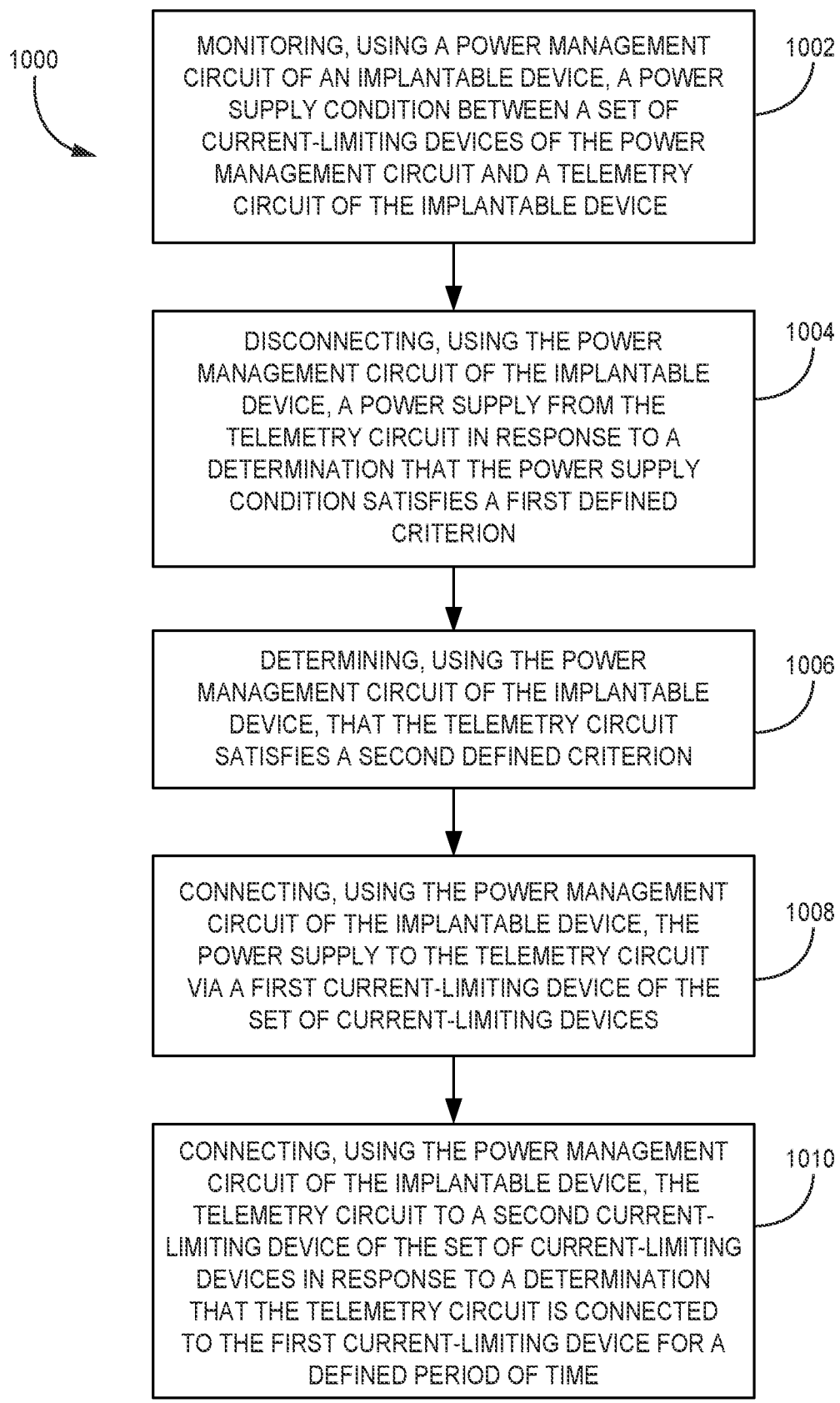

Referring now to FIG. 10, shown is a flow diagram of an example method 1000 facilitating improved power management of an implantable device in accordance with yet another embodiment. In some embodiments of method 1000, an implantable device (e.g., implantable device 104) employs a power management circuit (e.g., power management circuit 204) in connection with a telemetry circuit (e.g., telemetry circuit 202) and/or a power source (e.g., power source 206) to facilitate improved power management of the implantable device. Repetitive description of like elements employed in other embodiments described herein is omitted for sake of brevity.

At 1002, using a power management circuit of an implantable device (e.g., using the power management circuit 204), a power supply condition between a set of current-limiting devices of the power management circuit and a telemetry circuit of the implantable device is monitored. For example, a power supply condition between the set of current-limiting devices of the power management circuit and the telemetry circuit of the implantable device can be repeatedly monitored. The power supply condition can include, for example, a voltage condition, a current condition and/or another electrical characteristic.

At 1004, using the power management circuit of the implantable device (e.g., using the power management circuit 204), a power supply is disconnected from the telemetry circuit in response to a determination that the power supply condition satisfies a first defined criterion. For example, the power supply can be disconnected from the telemetry circuit in response to a determination that the power supply condition is above or below a defined threshold value for the power supply condition.

At 1006, using the power management circuit of the implantable device (e.g., using the power management circuit 204), it can be determined that the telemetry circuit satisfies a second defined criterion. For example, it can be determined that a telemetry session (e.g., a telemetry session related to broadcasting one or more data packets and/or communicating with respect to an external device) is being initiated by the telemetry circuit previously disconnected from the power supply.

At 1008, using the power management circuit of the implantable device (e.g., using the power management circuit 204), the power supply is connected to the telemetry circuit via a first current-limiting device of the set of current-limiting devices. For example, a first current-limiting device associated with a first resistance can be connected to the telemetry circuit to allow current from the power supply to be provided to the telemetry circuit.

At 1010, using the power management circuit of the implantable device (e.g., using the power management circuit 204), the telemetry circuit is connected to a second current-limiting device of the set of current-limiting devices in response to a determination that the telemetry circuit is connected to the first current-limiting device for a defined period of time. For example, in response to a determination that the telemetry circuit is connected to the first current-limiting device for a defined period of time, a second current-limiting device associated with a second resistance that is different than the first resistance can be connected to the telemetry circuit to allow a different amount of the current from the power supply to be provided to the telemetry circuit.

Figure 11:
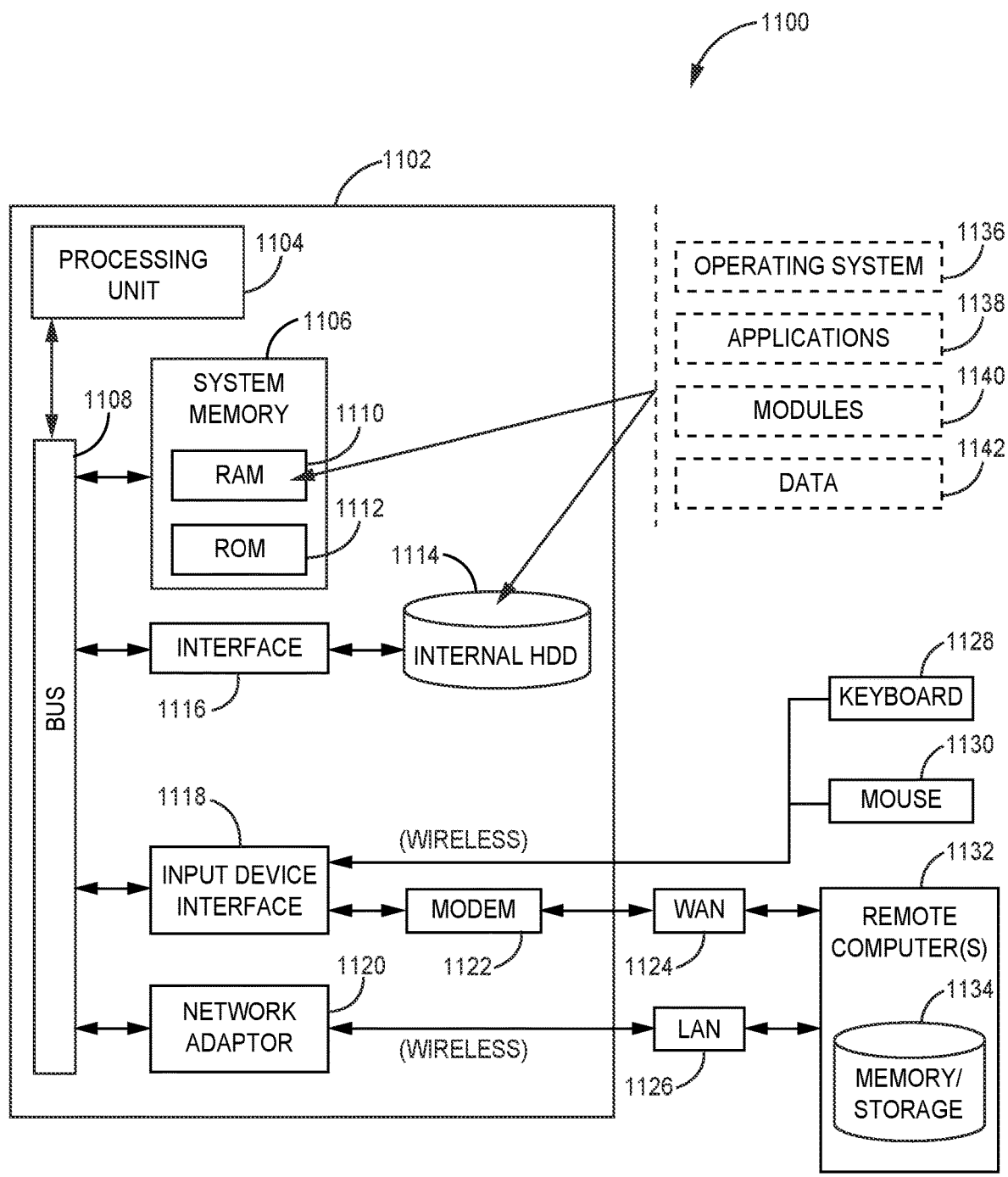
FIG. 11 illustrates a block diagram of an example, non-limiting computer operable to facilitate improved power management of an implantable device in accordance with one or more embodiments described herein.

FIG. 11 illustrates a block diagram of a computer operable to facilitate improved power management of an implantable device in accordance with one or more embodiments described herein. For example, in some embodiments, the computer can be or be included within implantable device 104 and/or external device 116 (or any component of the implantable device 104 and/or external device 116). Repetitive description of like elements employed in other embodiments described herein is omitted for sake of brevity.

In order to provide additional context for one or more embodiments described herein, FIG. 11 and the following discussion are intended to provide a brief, general description of a suitable computing environment 1100 in which the one or more embodiments described herein can be implemented.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices, e.g., via access requests, queries or other data retrieval protocols, for a variety of operations with respect to the information stored by the medium.

In this regard, the term "tangible" herein as applied to storage, memory, computer-readable media or computer-readable storage media, is to be understood to exclude only propagating intangible signals per se as a modifier and does not relinquish coverage of all standard storage, memory, computer-readable media or computer-readable storage media that are not only propagating intangible signals per se. In this regard, the term "non-transitory" herein as applied to storage, memory, computer-readable media or computer-readable storage media, is to be understood to exclude only propagating transitory signals per se as a modifier and does not relinquish coverage of all standard storage, memory, computer-readable media or computer-readable storage media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of the data signal's characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 11, example environment 1100 for implementing one or more embodiments of the embodiments described herein includes computer 1102, computer 1102 including processing unit 1104, system memory 1106 and system bus 1108. System bus 1108 couples system components including, but not limited to, system memory 1106 to processing unit 1104. Processing unit 1104 can be any of various commercially available processors. Dual microprocessors and other multi processor architectures can also be employed as processing unit 1104.

System bus 1108 can be any of several types of bus structure that can further interconnect to a memory bus (with or without a memory controller), a peripheral bus, and a local bus using any of a variety of commercially available bus architectures. System memory 1106 includes RAM 1110 and ROM 1112. A basic input/output system (BIOS) can be stored in a non-volatile memory such as ROM, erasable programmable read only memory (EPROM), EEPROM, which BIOS contains the basic routines that help to transfer information between elements within computer 1102, such as during startup. RAM 1110 can also include a high-speed RAM such as static RAM for caching data.

Computer 1102 further includes internal hard disk drive (HDD) 1114 (e.g., Enhanced Integrated Drive Electronics (EIDE), Serial Advanced Technology Attachment (SATA)). HDD 1114 can be connected to system bus 1108 by hard disk drive interface 1116. The drives and their associated computer-readable storage media provide nonvolatile storage of data, data structures, computer-executable instructions, and so forth. For computer 1102, the drives and storage media accommodate the storage of any data in a suitable digital format.

A number of program modules can be stored in the drives and RAM 1110, including operating system 1136, one or more application programs 1138, other program modules 1140 and program data 1142. All or portions of the operating system, applications, modules, and/or data can also be cached in RAM 1110. The systems and methods described herein can be implemented utilizing various commercially available operating systems or combinations of operating systems.

A mobile device can enter commands and information into computer 1102 through one or more wireless input devices, e.g., wireless keyboard 1128 and a pointing device, such as wireless mouse 1130. Other input devices (not shown) can include a smart phone, tablet, laptop, wand, wearable device or the like. These and other input devices are often connected to the processing unit 1104 through input device interface 1118 that can be coupled to system bus 1108, but can be connected by other interfaces, such as a parallel port, an IEEE serial port, a game port and/or a universal serial bus (USB) port.

Computer 1102 can operate in a networked environment using logical connections via wired and/or wireless communications to one or more remote computers, such as remote computer(s) 1132. Remote computer(s) 1132 can be a workstation, a server computer, a router, a personal computer, portable computer, microprocessor-based entertainment appliance, a peer device or other common network node, and typically includes many or all of the elements described relative to computer 1102, although, for purposes of brevity, only memory/storage device 1134 is illustrated. The logical connections depicted include wired/wireless connectivity to a local area network (LAN) 1126 and/or larger networks, e.g., WAN 1124, as well as smaller PANs involving a few devices (e.g., at least two). LAN and WAN networking environments are commonplace in the home, offices (e.g., medical facility offices, hospital offices) and companies, and facilitate enterprise-wide computer networks, such as intranets, all of which can connect to a global communications network (e.g., the Internet).

When used in a LAN networking environment, computer 1102 can be connected to local network through a wired and/or wireless communication network interface or adapter 1120. Adapter 1120 can facilitate wired or wireless communication to LAN 1126, which can also include a wireless access point (AP) connected to the LAN 1126 for communicating with adapter 1120.

When used in a WAN networking environment, computer 1102 can include modem 1122 or can be connected to a communications server on WAN 1124 or has other means for establishing communications over WAN 1124, such as by way of the Internet. Modem 1122, which can be internal or external and a wired or wireless device, can be connected to system bus 1108 via input device interface 1118. In a networked environment, program modules depicted relative to computer 1102 or portions thereof, can be stored in a remote memory/storage device. It will be appreciated that the network connections shown are example and other means of establishing a communications link between the computers can be used.

Computer 1102 can be operable to communicate with any wireless devices or entities operatively disposed in wireless communication via any number of protocols, including, but not limited to, NFC, Wi-Fi and/or BLUETOOTH® wireless protocols. Thus, the communication can be a defined structure as with a conventional network or simply an ad hoc communication between at least two devices.

NFC can allow point-to-point connection to an NFC-enabled device in the NFC field of an IMD within the home or at any location. NFC technology can be facilitated using an NFC-enabled smart phone, tablet or other device that can be brought within 3-4 centimeters of an implanted NFC component. NFC typically provides a maximum data rate of 424 kilobits per second (Kbps), although data rates can range from 6.67 Kbps to 828 Kbps. NFC typically operates at the frequency of 13.56 megahertz (MHz). NFC technology communication is typically over a range not exceeding 0.2 meters (m) and setup time can be less than 0.1 seconds. Low power (e.g., 15 milliamperes (mAs)) reading of data can be performed by an NFC device. Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 10BaseT wired Ethernet networks used in many offices.

The embodiments of devices described herein can employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out one or more embodiments thereof. Moreover, the classifier can be employed to determine a ranking or priority of each cell site of an acquired network. A classifier is a function that maps an input attribute vector, x=(x1, x2, x3, x4, . . . , xn), to a confidence that the input belongs to a class, that is, f(x)=confidence (class). Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a predetermined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of mobile device equipment. A processor can also be implemented as a combination of computing processing units.

Memory disclosed herein can include volatile memory or nonvolatile memory or can include both volatile and nonvolatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages, databases) of the embodiments is intended to include, without being limited to, these and any other suitable types of memory.

As used herein, terms such as "data storage," "database," and substantially any other information storage component relevant to operation and functionality of a component, refer to "memory components," or entities embodied in a "memory" or components including the memory. It will be appreciated that the memory components or computer-readable storage media, described herein can be either volatile memory or nonvolatile memory or can include both volatile and nonvolatile memory.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

What has been described above includes mere examples of one or more embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An implantable device configured to be at least partially implanted within a patient, comprising:
   a housing configured to be implanted at least partially within the patient;
   a memory within the housing;
   circuitry, within the housing, and configured to at least one of obtain sensed physiological data associated with the patient or deliver a therapy to the patient;
   a telemetry circuit configured to facilitate a telemetry session between the implantable device and an external device; and a power management circuit configured to determine that a telemetry circuit of the implantable device satisfies a first defined criterion, disconnect the telemetry circuit from a power source of the implantable device, wherein the disconnecting is performed based on the determining that the telemetry circuit satisfies the first defined criterion, determine that the telemetry circuit satisfies a second defined criterion, and connect the power source to the telemetry circuit via a first current-limiting device of the power management circuit, wherein the connecting is performed based on the determining that the telemetry circuit satisfies the second defined criterion.

2. The implantable device of claim 1, wherein the power management circuit is configured to determine that the telemetry circuit of the implantable device satisfies the first defined criterion based on a determination that the telemetry circuit is not communicating with an external device.

3. The implantable device of claim 2, wherein the power management circuit is configured to determine that the telemetry circuit is not communicating with the external device based on a voltage level associated with the telemetry circuit.

4. The implantable device of claim 2, wherein the power management circuit is configured to determine that the telemetry circuit is not communicating with the external device based on a determination that a voltage level associated with the telemetry circuit is below a defined threshold value.

5. The implantable device of claim 1, wherein the power management circuit is further configured to disconnect the telemetry circuit from the power source of the implantable device further based on a determination that the telemetry circuit is not broadcasting an advertising data packet.

6. The implantable device of claim 1, wherein the power management circuit is configured to determine that the telemetry circuit satisfies a second defined criterion based on a determination that the telemetry circuit is disconnected from the power source of the implantable device for a first defined period of time.

7. The implantable device of claim 6, wherein the power management circuit is further configured to connect the telemetry circuit to a second current-limiting device based on a determination that the telemetry circuit is connected to the first current-limiting device for a second defined period of time.

8. The implantable device of claim 1, wherein the first defined criterion is associated with a telemetry session with an external device.

9. The implantable device of claim 1, wherein the power management circuit comprises a soft-start sequence device comprising the first current-limiting device and a second current-limiting device.

10. The implantable device of claim 1, wherein the power management circuit is further configured to connect the telemetry circuit to a third current-limiting device based on a determination that the telemetry circuit is connected to the second current-limiting device for a third defined period of time.

11. A method, comprising:
determining, using a power management circuit of an implantable device, that a telemetry circuit of the implantable device satisfies a first defined criterion;
disconnecting, using the power management circuit of the implantable device, the telemetry circuit from a power source of the implantable device, wherein the disconnecting is performed based on the determining that the telemetry circuit satisfies the first defined criterion;
determining, using the power management circuit of the implantable device, that the telemetry circuit satisfies a second defined criterion; and
connecting, using the power management circuit of the implantable device, the power source to the telemetry circuit via a first current-limiting device of the power management circuit, wherein the connecting is performed based on the determining that the telemetry circuit satisfies the second defined criterion.

12. The method of claim 11 wherein determining that the telemetry circuit of the implantable device satisfies a first defined criterion comprises determining that the telemetry circuit is not communicating with an external device.

13. The method of claim 12 further comprising determining that the telemetry circuit is not communicating with the external device based on a voltage level associated with the telemetry circuit.

14. The method of claim 12 wherein determining that the telemetry circuit is not communicating with the external device comprises determining that a voltage level associated with the telemetry circuit is below a defined threshold value.

15. The method of claim 11 wherein disconnecting, using the power management circuit of the implantable device, the telemetry circuit from the power source of the implantable device comprises determining that the telemetry circuit is not broadcasting an advertising data packet.

16. The method of claim 11, wherein determining that the telemetry circuit satisfies a second defined criterion comprises determining that the telemetry circuit is disconnected from the power source of the implantable device for a first defined period of time.

17. The method of claim 16, further comprising connecting, using the power management circuit of the implantable device, the telemetry circuit to a second current-limiting device based on a determination that the telemetry circuit is connected to the first current-limiting device for a second defined period of time.

18. The method of claim 11 wherein the first defined criterion is associated with a telemetry session with an external device.

19. An apparatus, comprising:
a telemetry circuit configured to perform a telemetry session associated with a device;
a power source configured to provide power to the telemetry circuit; and
a power management circuit configured to determine that a telemetry circuit of the implantable device satisfies a first defined criterion, disconnect the telemetry circuit from a power source of the implantable device, wherein the disconnecting is performed based on the determining that the telemetry circuit satisfies the first defined criterion, determine that the telemetry circuit satisfies a second defined criterion, and connect the power source to the telemetry circuit via a first current-limiting device of the power management circuit, wherein the connecting is performed based on the determining that the telemetry circuit satisfies the second defined criterion.

20. A system, comprising:
an implantable device comprising:
a telemetry circuit configured to broadcast one or more advertising data packets; and
a power management circuit configured to determine that a telemetry circuit of the implantable device satisfies a first defined criterion, disconnect the telemetry circuit from a power source of the implantable device, wherein the disconnecting is performed based on the determining that the telemetry circuit satisfies the first defined criterion, determine that the telemetry circuit satisfies a second defined criterion, and connect the power source to the telemetry circuit via a first current-limiting device of the power management circuit, wherein the connecting is performed based on the determining that the telemetry circuit satisfies the second defined criterion; and an external device configured to perform telemetry communication with the implantable device based on the one or more advertising data packets.

* * * * *